United States Patent
Nagarathnam et al.

(10) Patent No.: US 6,924,290 B2
(45) Date of Patent: *Aug. 2, 2005

(54) RHO-KINASE INHIBITORS

(75) Inventors: Dhanapalan Nagarathnam, Bethany, CT (US); Jacques Dumas, Bethany, CT (US); Holia Hatoum-Mokdad, Hamden, CT (US); Stephen Boyer, Fairfield, CT (US); Chunguang Wang, Hamden, CT (US); Hans Pluempe, Wuppertal (DE); Achim Feurer, Wilhelmsfeld (DE); Samir Bennabi, Wuppertal (DE)

(73) Assignee: Bayer Pharmaceuticals Corporation, West Haven, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/349,177

(22) Filed: Jan. 23, 2003

(65) Prior Publication Data

US 2004/0002508 A1 Jan. 1, 2004

Related U.S. Application Data

(60) Provisional application No. 60/349,987, filed on Jan. 23, 2002.

(51) Int. Cl.[7] .................... A61K 31/505; C07D 239/48
(52) U.S. Cl. .................... 514/258.1; 514/275; 544/323; 544/324; 544/325; 544/253
(58) Field of Search ............................. 544/323, 324, 544/325, 253; 514/258.1, 275

(56) References Cited

U.S. PATENT DOCUMENTS

| | | |
|---|---|---|
| 4,642,347 A | 2/1987 | Kreft, III et al. |
| 4,952,567 A | 8/1990 | DeMeyts et al. |
| 5,240,940 A | 8/1993 | Arnold et al. |
| 5,245,036 A | 9/1993 | Robey et al. |
| 5,324,839 A | 6/1994 | Clemence et al. |
| 5,478,938 A | 12/1995 | Clemence et al. |
| 5,817,674 A | 10/1998 | Clemence et al. |
| 5,840,695 A | 11/1998 | Frank et al. |
| 5,885,803 A | 3/1999 | Bandman et al. |
| 5,906,819 A | 5/1999 | Kaibuchi et al. |
| 5,932,470 A | 8/1999 | Frank et al. |
| 5,958,944 A | 9/1999 | Arita et al. |
| 5,972,598 A | 10/1999 | Chaudhary et al. |
| 5,977,102 A | 11/1999 | Himmelsbach et al. |
| 6,004,979 A | 12/1999 | Clemence et al. |
| 6,153,617 A | 11/2000 | Bridges |
| 6,184,226 B1 | 2/2001 | Chakravarty et al. |
| 6,207,148 B1 | 3/2001 | Bandman et al. |
| 6,218,410 B1 | 4/2001 | Uehata et al. |
| 6,277,989 B1 | 8/2001 | Chakravarty et al. |
| 6,326,373 B1 | 12/2001 | Uckun et al. |
| 6,391,874 B1 | 5/2002 | Cockerill et al. |
| 2001/0014679 A1 | 8/2001 | Tang et al. |
| 2001/0044442 A1 | 11/2001 | Uckun et al. |
| 2002/0055514 A1 | 5/2002 | Uckun et al. |

FOREIGN PATENT DOCUMENTS

| | | |
|---|---|---|
| EP | 1 034 793 A1 | 9/2000 |
| EP | 1 163 910 A1 | 12/2001 |
| EP | 1 174 150 A1 | 1/2002 |
| EP | 1 177 796 A1 | 2/2002 |
| WO | WO 96/40142 | 12/1996 |
| WO | WO 97/03069 A1 | 1/1997 |
| WO | WO 98/02434 A1 | 1/1998 |
| WO | WO 98/02438 | 1/1998 |
| WO | WO 99/23113 A2 | 5/1999 |
| WO | WO 99/24440 | 5/1999 |
| WO | WO 99/35132 A1 | 7/1999 |
| WO | WO 99/35146 A1 | 7/1999 |
| WO | WO 99/65908 A1 | 12/1999 |
| WO | WO 00/12497 A2 | 3/2000 |
| WO | WO 00/13497 | 3/2000 |
| WO | WO 00/39101 A1 | 7/2000 |
| WO | WO 00/55162 A2 | 9/2000 |
| WO | WO 00/57914 A1 | 10/2000 |
| WO | WO 01/09134 A1 | 2/2001 |
| WO | WO 01/28561 A1 | 4/2001 |
| WO | WO 02/24667 A1 | 3/2002 |
| WO | WO 02/30465 A2 | 4/2002 |
| WO | WO 02/053143 A2 | 7/2002 |

OTHER PUBLICATIONS

Blackburn et al., chemical Abstracts, vol. 138:321291, 2003.*
Gour et al., Chemical Abstracts, vol. 137:363033, 2002.*
Chemical Abstract No. 117:251318p "Novel piperazinyl-substituted pyrimidines as antihypertensive and vasodilators", no year.

* cited by examiner

*Primary Examiner*—Richard L. Raymond
(74) *Attorney, Agent, or Firm*—Millen White Zelano & Branigan P.C.

(57) ABSTRACT

Disclosed are compounds and derivatives thereof, their synthesis, and their use as Rho-kinase inhibitors. These compounds are useful for inhibiting tumor growth, treating erectile dysfunction, and treating other indications mediated by Rho-kinase, e.g., coronary heart disease.

17 Claims, No Drawings

RHO-KINASE INHIBITORS

This application claims the benefit of U.S. provisional application Ser. No. 60/349,987, filed Jan. 23, 2002.

FIELD OF THE INVENTION

The present invention relates to compounds and derivatives thereof, their synthesis, and their use as Rho-kinase inhibitors. These compounds of the present invention are useful for inhibiting tumor growth, treating erectile dysfunction, and treating other indications mediated by Rho-kinase, e.g., coronary heart disease.

BACKGROUND

The pathology of a number of human and animal diseases including hypertension, erectile dysfunction, coronary cerebral circulatory impairments, neurodegenerative disorders and cancer can be linked directly to changes in the actin cytoskeleton. These diseases pose a serious unmet medical need. The actin cytoskeleton is composed of a meshwork of actin filaments and actin-binding proteins found in all eukaryotic cells. In smooth muscle cells the assembly and disassembly of the actin cytoskeleton is the primary motor force responsible for smooth muscle contraction and relaxation. In non-muscle cells, dynamic rearrangements of the actin cytoskeleton are responsible for regulating cell morphology, cell motility, actin stress fiber formation, cell adhesion and specialized cellular functions such as neurite retraction, phagocytosis or cytokinesis (Van Aelst, et al. *Genes Dev* 1997, 11, 2295).

The actin cytoskeleton is controlled by a family of proteins that are a subset of the Ras superfamily of GTPases. This subset currently consists of RhoA through E and RhoG (refereed to collectively as Rho), Rac 1 and 2, Cdc42Hs and G25K and TC10 isoforms (Mackay, et al. *J Biol Chem* 1998, 273, 20685). These proteins are GTP (guanine nucleotide triphosphate) binding proteins with intrinsic GTPase activity. They act as molecular switches and cycles between inactive GDP (guanine nucleotide diphosphate) bound and active GTP bound states. Using biochemical and genetic manipulations, it has been possible to assign functions to each family member. Upon activation the Rho proteins controls the formation of actin stress fibers, thick bundles of actin filaments, and the clustering of integrins at focal adhesion complexes. When activated the Rac proteins control the formation of lamellopodia or membrane ruffles on the cell surface and Cdc42 controls filopodia formation. Together this family of proteins plays a critical part in the control of key cellular functions including cell movement, axonal guidance, cytokinesis, and changes in cell morphology, shape and polarity.

Depending on the cell type and the activating receptor, the Rho proteins can control different biological responses. In smooth muscle cells, Rho proteins are responsible for the calcium sensitization during smooth muscle contraction. In non-smooth muscle cells the Rho GTPases are responsible for the cellular responses to agonist such as lysophosphatidic acid (LPA), thrombin and thromboxane $A_2$ (Fukata, et al. *Trends Pharcol Sci* 2001, 22, 32). Agonist response is coupled through heterotrimeric G proteins $G_{alpha\ 12}$ or $G_{alpha\ 13}$ (Goetzl, et al. *Cancer Res* 1999, 59, 4732; Buhl, et al. *J Biol Chem* 1995, 270, 24631) though other receptors may be involved. Upon activation Rho GTPases activate a number of downstream effectors including PIP5-kinase, Rhothekin, Rhophilin, PKN and Rho kinase isoforms ROCK-1/ROKbeta and ROCK-1/ROKalpha (Mackay and Hall *J Biol Chem* 1998, 273, 20685; Aspenstrom *Curr Opin Cell Biol* 1999, 11, 95; Amano, et al. *Exp Cell Res* 2000, 261, 44).

Rho kinase was identified as a RhoA interacting protein isolated from bovine brain (Matsui, et al. *Embo J* 1996, 15, 2208). It is a member of the myotonic dystrophy family of protein kinase and contains a serine/threonine kinase domain at the amino terminus, a coiled-coil domain in the central region and a Rho interaction domain at the carboxy terminus (Amano, et al. *Exp Cell Res* 2000, 261, 44). Its kinase activity is enhanced upon binding to GTP-bound RhoA and when introduced into cells, it can reproduce many of the activities of activated RhoA. In smooth muscle cells Rho kinase mediates calcium sensitization and smooth muscle contraction and inhibition of Rho kinase blocks 5-HT and phenylephrine agonist induced muscle contraction. When introduced into non-smooth muscle cells, Rho kinase induces stress fiber formation and is required for the cellular transformation mediated by RhoA (Sahai, et al. *Curr Biol* 1999, 9, 136). Rho kinase regulates a number of downstream proteins through phosphorylation, including myosin light chain (Somlyo, et al. *J Physiol (Lond)* 2000, 522 Pt 2, 177), the myosin light chain phosphatase binding subunit (Fukata, et al. *J Cell Biol* 1998, 141, 409) and LIM-kinase 2 (Sumi, et al. *J Bio Chem* 2001, 276, 670).

Inhibition of Rho kinase activity in animal models has demonstrated a number of benefits of Rho kinase inhibitors for the treatment of human diseases. Several patents have appeared claiming (+)-trans-4-(1-aminoethyl)-1-(pyridin-4-ylaminocarbonyl)cyclohexane dihydrochloride monohydrate (WO-0007835 1, WO-00057913) and substituted isoquinolinesulfonyl (EP-00187371) compounds as Rho kinase inhibitors with activity in animal models. These include models of cardiovascular diseases such as hypertension (Uehata, et al. *Nature* 1997, 389, 990), atherosclerosis (Retzer, et al. *FEBS Lett* 2000, 466, 70), restenosis (Eto, et al. *Am J Physiol Heart Circ Physiol* 2000, 278, H1744; Negoro, et al. *Biochem Biophys Res Commun* 1999, 262, 211), cerebral ischemia (Uehata, et al. *Nature* 1997, 389, 990; Seasholtz, et al. *Circ Res* 1999, 84, 1186; Hitomi, et al. *Life Sci* 2000, 67, 1929; Yamamoto, et al. *J Cardiovasc Pharmacol* 2000, 35, 203), cerebral vasospasm (Sato, et al. *Circ Res* 2000, 87, 195; Kim, et al. *Neurosurgery* 2000, 46, 440), penile erectile dysfunction (Chitaley, et al. *Nat Med* 2001, 7, 119), central nervous system disorders such as neuronal degeneration and spinal cord injury (Hara, et al. *J Neurosurg* 2000, 93, 94; Toshima, et al. *Stroke* 2000, 31, 2245) and in neoplasias where inhibition of Rho kinase has been shown to inhibit tumor cell growth and metastasis (Itoh, et al. *Nat Med* 1999, 5, 221; Somlyo, et al. *Biochem Biophys Res Commun* 2000, 269, 652), angiogenesis (Uchida, et al. *Biochem Biophys Res Commun* 2000, 269, 633; Gingras, et al. *Biochem J* 2000, 348 Pt 2, 273), arterial thrombotic disorders such as platelet aggregation (Klages, et al. *J Cell Biol* 1999, 144, 745; Retzer, et al. *Cell Signal* 2000, 12, 645) and leukocyte aggregation (Kawaguchi, et al. *Eur J Pharmacol* 2000, 403, 203; Sanchez-Madrid, et al. *Embo J* 1999, 18, 501), asthma (Setoguchi, et al. *Br J Pharmacol* 2001, 132, 111; Nakahara, et al. *Eur J Pharmacol* 2000, 389, 103), regulation of intraoccular pressure (Honjo, et al. *Invest Ophthalmol Vis Sci* 2001, 42, 137) and bone resorption (Chellaiah, et al. *J Biol Chem* 2000, 275, 11993; Zhang, et al. *J Cell Sci* 1995, 108, 2285).

The inhibition of Rho kinase activity in patients has benefits for controlling cerebral vasospasms and ischemia following subarachnoid hemorrhage (*Pharma Japan* 1995, 1470, 16).

SUMMARY OF THE INVENTION

The compounds and their derivatives presented in this invention are useful as Rho Kinase inhibitors and thus have utilities in the treatment of cardiovascular disease, e.g., hypertension, atherosclerosis, restenosis, cerebral ischemia, and cerebral vasospasm, as well as neuronal degeneration, spinal cord injury, cancers of the breast, colon, prostate, ovaries, brain and lung and their metastases, thrombotic disorders, asthma, glaucoma and osteoporosis.

In addition, the compounds of the invention are useful to treat erectile dysfunction, i.e., erectile dysfunction mediated by Rho-kinase. Erectile dysfunction can be defined as an inability to obtain or sustain an erection adequate for intercourse, WO 94/28902, U.S. Pat. No. 6,103,765 and U.S. Pat. No. 6,124,461.

The invention involves compounds of formula I

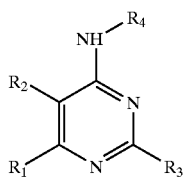

I wherein
- $R_1$ and $R_2$ are each independently H, halo, alkyl, optionally substituted by halo up to the perhalo level, cycloalkyl, alkenyl, alkynyl, $NO_2$, $NH_2$, $NR_6R_7$, or furyl, thienyl, pyridyl, trifluoromethyl or phenyl each optionally substituted with $NH_2$, $NO_2$, trifluoromethyl or alkoxy;
- $R_1$ and $R_2$ may be taken together to form a ring of from 5 to 7 members optionally interrupted by N and optionally substituted on N by benzyl;
- $R_3$ is $NH_2$ or —NH— phenyl optionally substituted with halo, $C_1$–$C_4$ alkyl, trifluoromethyl, nitro or amino;
- $R_4$ is

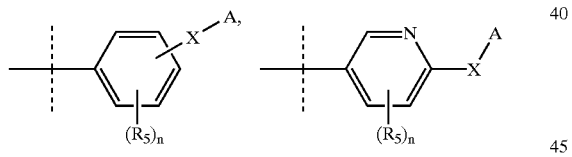

or indol-5-yl (optionally) substituted on the N with pyridyl;
- X is a linker substituted at the 3 or 4 position of the ring and is selected from O, S, —S—$CH_2$—, —$(CH_2)_m$—, or —(C=O)—;
- A is phenyl optionally substituted with alkylthio or OH, pyridyl, quinolyl or isoquinolyl;
- each $R_5$ independently is halo, alkyl optionally substituted by halo up to the perhalo level, cycloalkyl, alkoxy, alkenyl, alkynyl, $NO_2$, $NH_2$, or trifluoromethyl;
- n is 0,1,2,3 or 4;
- m is 1 or 2; and
- $R_6$ and $R_7$ are each independently H, alkyl, cycloalkyl, or phenyl optionally substituted with halo, $CF_3$, alkyl, nitro or amino; or
- $R_6$ and $R_7$ may form, together with the N atom to which they are attached, a heterocyclic ring optionally substituted with alkyl, optionally interrupted by O, or optionally fused to phenyl;

with the proviso that formula I does not include the following compounds:

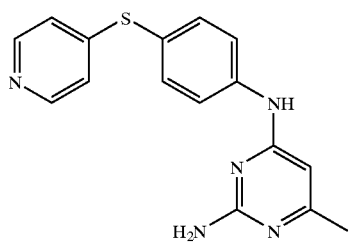

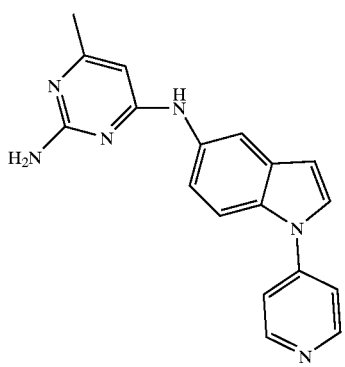

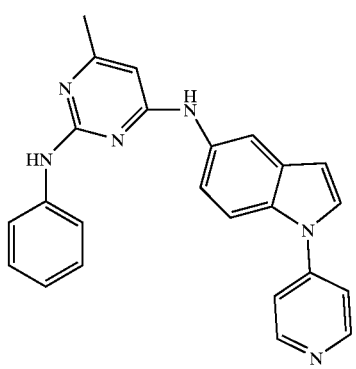

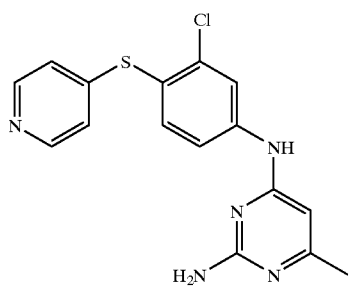

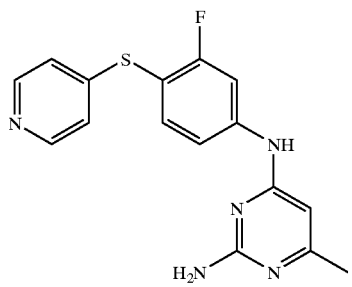

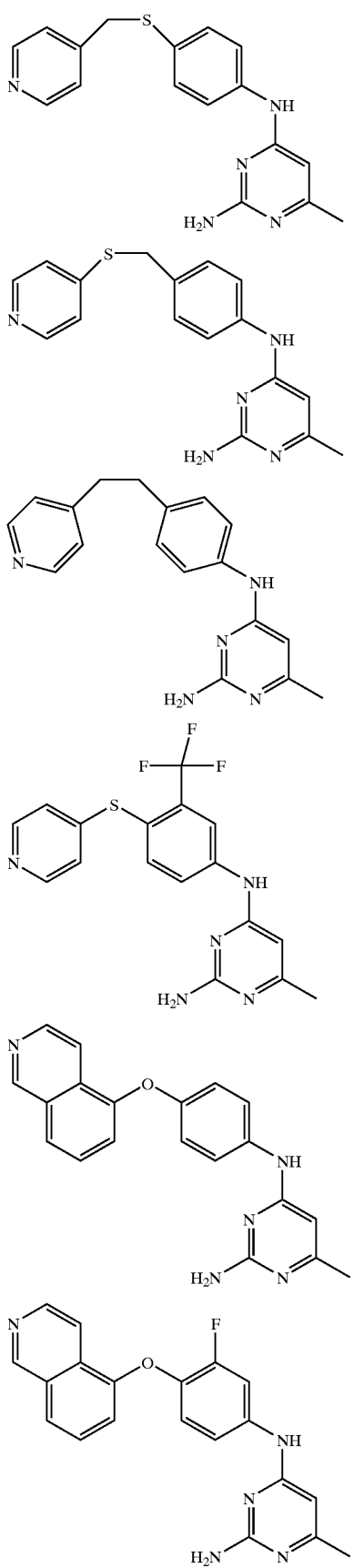
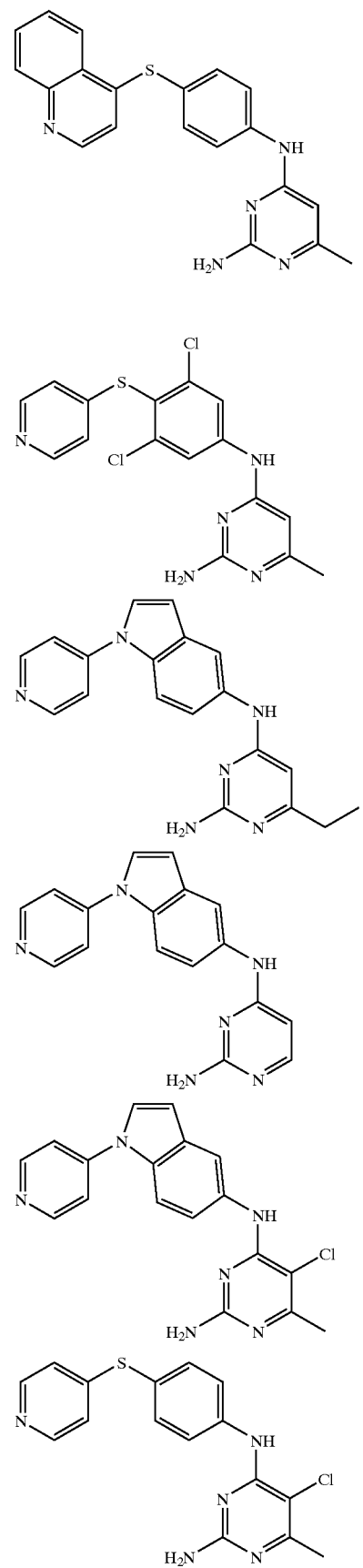

-continued
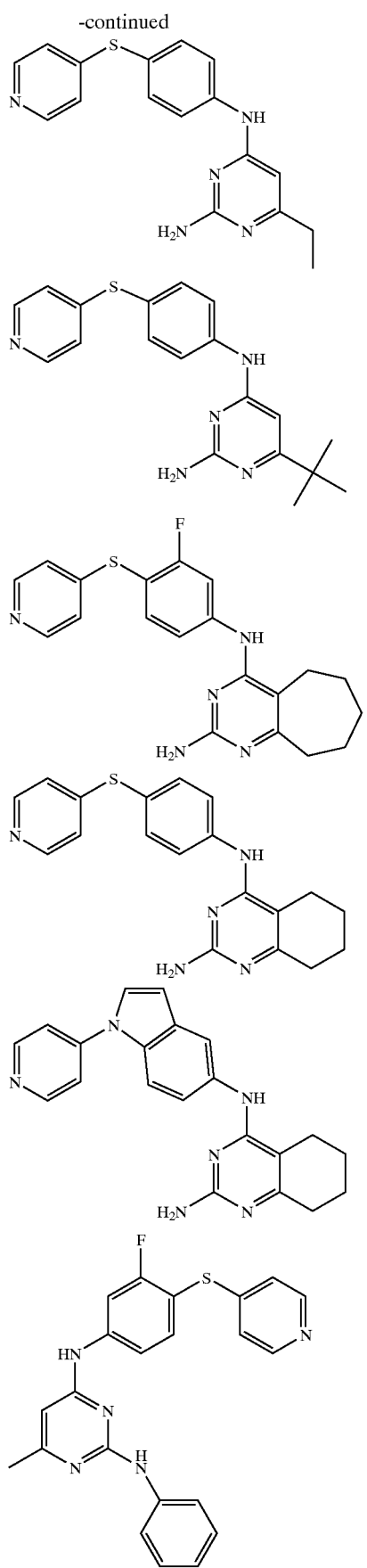
-continued
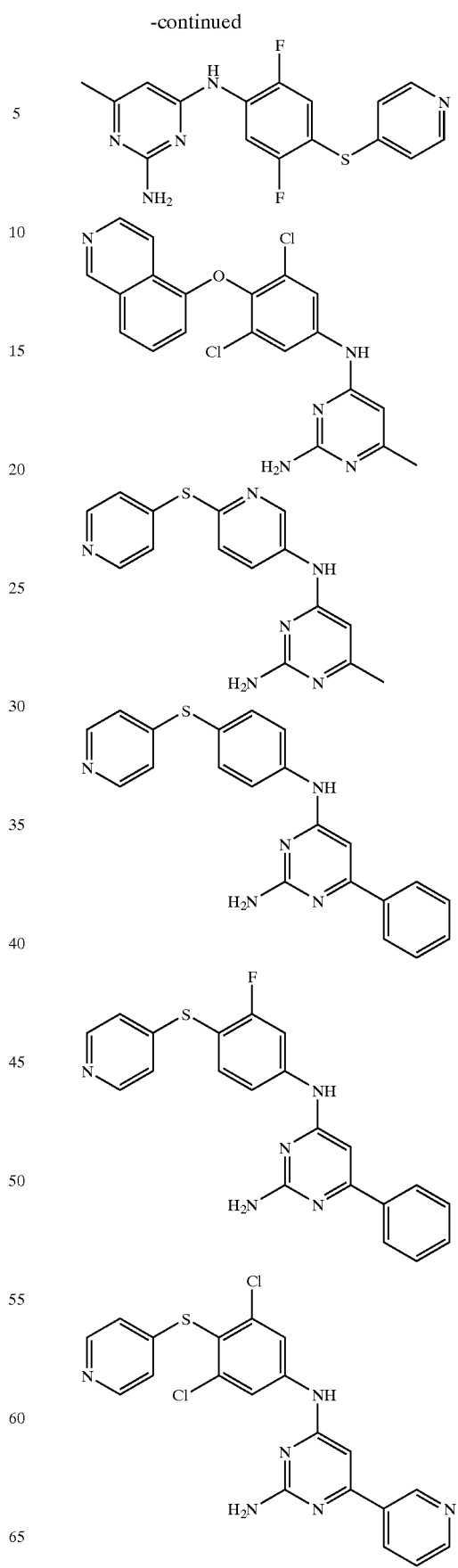

-continued
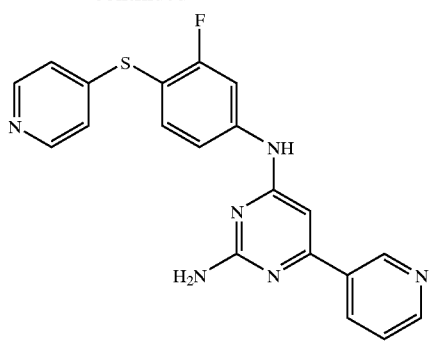
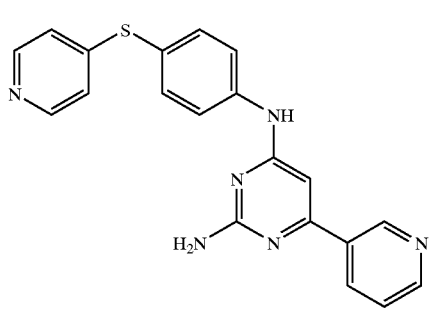
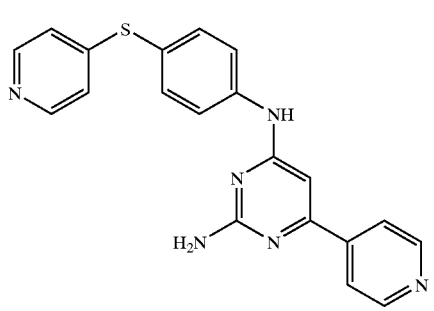
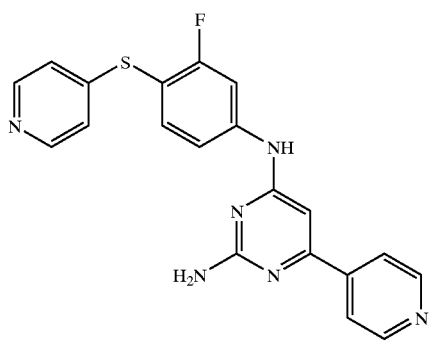
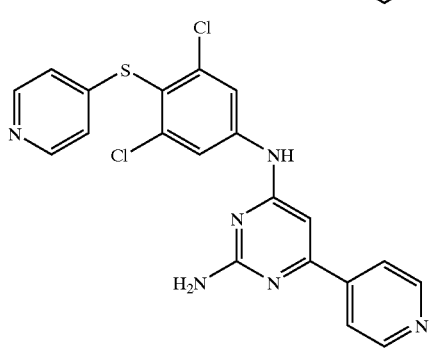
-continued
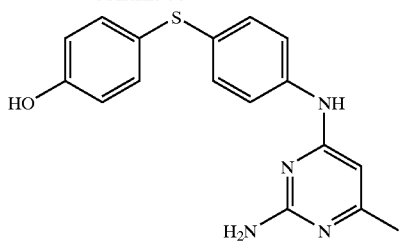
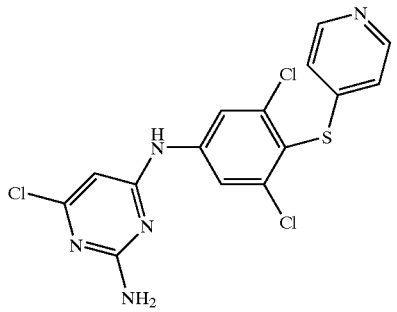
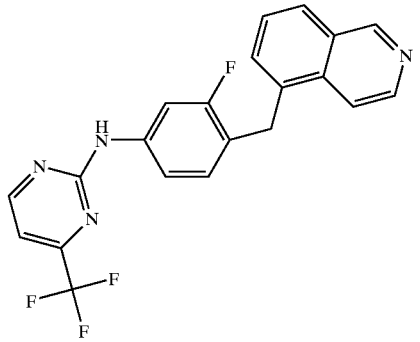
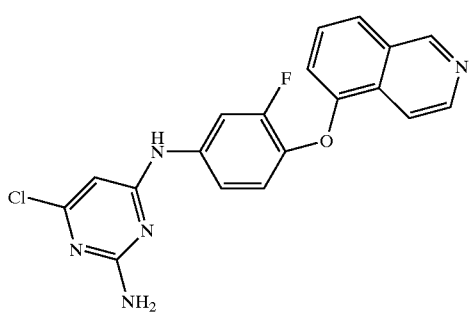
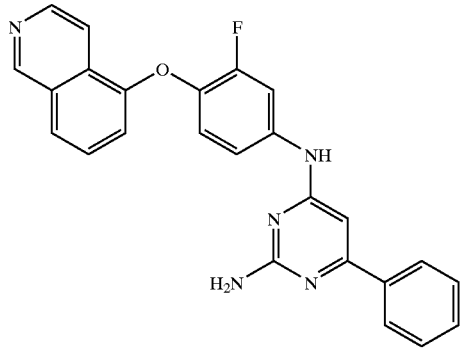

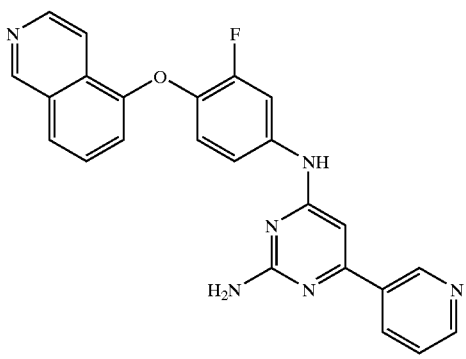

Preferred compounds of formula I include those wherein

R₁ and R₂ are each independently H, halo, C₁₋₁₂ alkyl optionally substituted by halo up to the perhalo level, C₂₋₁₂, alkenyl, C₂₋₁₂-alkynyl, NO₂, NH₂, NR₆R₇, alkyl, furyl thienyl, pyridyl, phenyl optionally substituted with NO₂, trifluoromethyl or NR₆R₇;

R₁ and R₂ may be taken together to form a ring of from 5 to 7 members optionally interrupted by N and (optionally) substituted on N by benzyl;

R₃ is NH₂ or —NH— phenyl optionally substituted with halo, C₁–C₄ alkyl, trifluoromethyl, nitro or amino;

R₄ is or indol-5-yl (optionally) substituted on the N with pyridyl;

X is a linker substituted at the 3 or 4 position of the ring and is selected from O, S, —S—CH₂—, —CH₂—S—, —(CH₂)ₘ—, or —(C=O)—;

A is phenyl optionally substituted by C₁₋₄ alkylthio or OH, pyridyl, quinolyl or isoquinolyl;

each $R_5$ independently is halo, $C_1$–$C_{12}$ alkyl, optionally substituted by halo, up to the perhalo level, $C_{2-12}$-alkenyl, $C_{2-12}$-alkynyl, $NO_2$, $NH_2$ or trifluoromethyl;

n is 0, 1, 2, 3 or 4;

m is 1 or 2; and $R_6$ and $R_7$ are each independently H, $C_1$–$C_6$ alkyl, or phenyl optionally substituted with halo, $CF_3$, $C_1$–$C_4$ alkyl, nitro or amino, with the exception of the compounds previously cited.

Particularly preferred compounds include those wherein
(i) X is not S or A is not pyridyl, or both;
(ii) X is not S or —S—$CH_2$—;
(iii) n is 1–4
(iv) n is 1–4 and each $R_5$ is independently is halo, $C_3$–$C_{12}$ alkyl optionally substituted by halo up to the perhalo level, $C_{2-12}$-alkenyl, $C_{2-12}$-alkynyl, $NO_2$, $NH_2$ or trifluoromethyl; or
(v) the compound of formula I is not

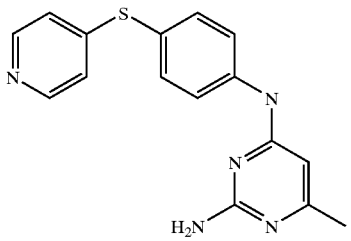

The terms identified above have the following meaning throughout:

"Alkyl" means straight or branched chain alkyl groups having from one to about twelve carbon atoms. Such groups include methyl, ethyl, n-propyl, isopropyl, n-butyl, isobutyl, sec-butyl, tert-butyl, n-pentyl, neo-pentyl, 2-pentyl, n-hexyl, 2-hexyl, 3-hexyl, dodecyl, 2,3-dimethylbutyl and the like.

"Cycloalkyl" means saturated monocyclic alkyl groups of from 3 to about 8 carbon atoms and includes such groups as cyclopropyl, cyclopentyl, cyclohexyl and the like.

"Alkenyl" means straight or branched chain alkenyl groups having from two to about twelve carbon atoms. Such groups include vinyl, allyl, isopropenyl, 3-butenyl and the like.

"Alkynyl" means straight or branched chain alkynyl groups having from two to about twelve carbon atoms. Such groups include ethynyl, propargyl, 3-pentynyl, 3-heptynyl, 1-methyl-2-butynyl and the like.

"Alkoxy" means straight or branched chain alkoxy groups having from about one to eight carbon atoms and includes such groups as methoxy, ethoxy, n-propoxy, isopropoxy, n-butoxy, isobutoxy, sec-butoxy, tert-butoxy and the like.

"Halo" means fluoro, chloro, bromo, or iodo. Preferred are fluoro, chloro and bromo, more preferably fluoro and chloro.

When an alkyl substituent is described as being substituted by oxo, it means substitution by a doubly bonded oxygen atom, which forms together with the carbon to which it is attached, a carbonyl group —(C=O)—.

The term "optionally substituted" means that the moiety so modified may be unsubstituted or substituted with the identified substituent(s).

When any moiety is described as being substituted, it can have one or more of the indicated substituents that can be located at any available position on the moiety. When there are two or more substituents on any moiety, each substituent is defined independently of any other substituent and can, accordingly, be the same or different.

The compounds of the Formula I can be made according to routine, conventional chemical methods, and/or as disclosed below, from starting materials which are either commercially available or producible according to routine, conventional chemical methods. General methods for the preparation of the compounds are given below, and the preparation of representative compounds is specifically illustrated in the Examples.

General Methods of Preparation

Compounds of Formula I may be prepared using one of the general methods summarized below in Reaction Schemes 1–3, from either commercially available or readily prepared starting materials. Preparation of starting material is described in Reaction Schemes 4–6.

In the first methods, illustrated in Reaction Scheme 1, the reaction of a chloropyrimidine of Formula II with a substituted aromatic compound of Formula III, where R1–R4 are as defined above, may be accomplished under either basic or acidic conditions (Reaction Scheme 1).

Reaction Scheme 1

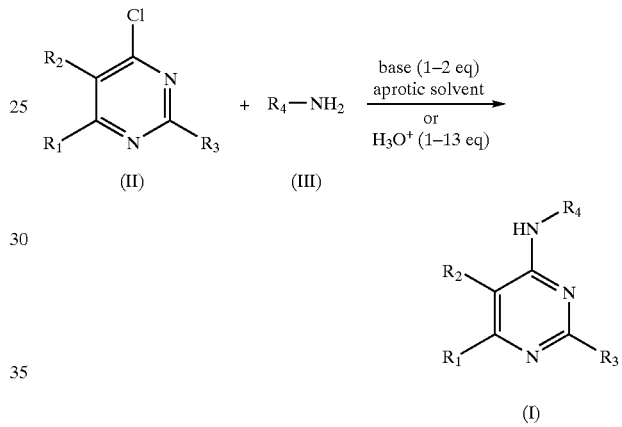

Alternatively, when $R_1$ is an aryl group, a two-step scheme may be employed. In the first step, the Formula III compound is allowed to react with the dichloropyrimidine of Formula IIa under acidic conditions as in Reaction Scheme 1. In the second step, the $R_1$ group is introduced by palladium-catalyzed coupling of a boronic acid of Formula $R_1B(OH)_2$ (e.g., Suzuki coupling) to provide compounds of Formula I in which $R_1$ is aryl (Reaction Scheme 2).

Reaction Scheme 2

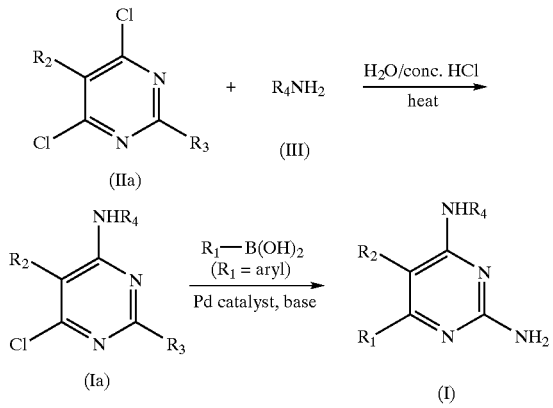

The compounds of Formula I, where $R_1$ is $NR_6R_7$, may be prepared conveniently by reaction the chloropyrimidine of Formula Ia with a variety of amines of Formula $R_6R_7NH$, usually in a higher boiling polar solvent such as n-butanol, and at an elevated temperature, e.g., 90–120° C. as shown in Reaction Scheme 3.

Reaction Scheme 3

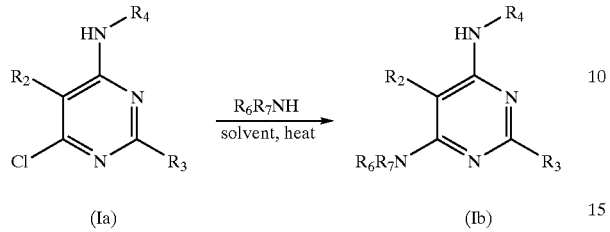

(Ia)   (Ib)

General Method of Preparation of Intermediates

Intermediate chloropyrimidines of Formula II and aryl amines of Formula III are either commercially available or may be prepared by methods well known in the art. For example, a pyrimidone can be converted to the corresponding chloropyrimidine II by reaction with $POCl_3$, and reduction of nitro aromatic compounds under standard conditions (e.g., Fe, HOAc) provides aryl amines of Formula III. Further illustrative methods are depicted in Reaction Schemes 4–6 below. For example, in Reaction Scheme 4, Formula III compounds in which $R_4$ is

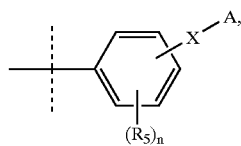

A is 2 or 4 pyridyl, and X is O or S, are prepared by a nucleophilic aromatic substitution reaction of a haloarene (A-halo) with a phenol or thiophenol of Formula IV, carried out in a polar solvent such as DMF and assisted by a base such as potassium carbonate (Reaction Scheme 4).

Reaction Scheme 4

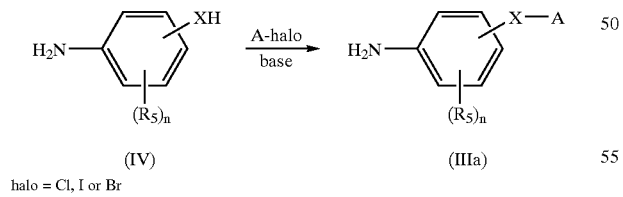

(IV)   (IIIa)

halo = Cl, I or Br

Intermediates of Formula IIIb may be prepared as shown in Reaction Scheme 5 in two steps from a nitroaromatic compound of Formula V, where Z represents either CH or N. The nitro aromatic compound is allowed to react in basic media at elevated temperatures, and the resulting nitro aromatic compound is reduced by standard means, e.g., iron and acetic acid.

Reaction Scheme 5

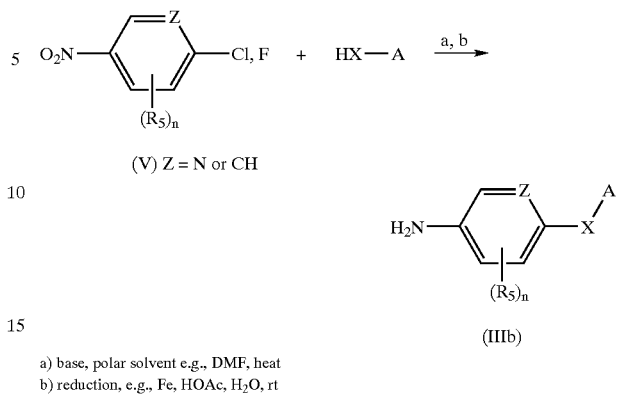

(V) Z = N or CH (IIIb)

a) base, polar solvent e.g., DMF, heat
b) reduction, e.g., Fe, HOAc, $H_2O$, rt

A wide variety of chloropyrimidines of Formula II where $R_3$ is $NH_2$ and $R_1$ is other than $NR_6R_7$, may be prepared by the route shown in Reaction Scheme 6 below. Reaction of a carboxylic acid of Formula VI, where $R_1$ is other than $NR_6R_7$, with a substituted Meldrum's acid of Formula VII (prepared, for example by alkylation of Meldrum's acid with $R_2$-halo and base), gives a ketoester of Formula VIII. The pyrimidone compound of Formula IX is formed by reaction of compound VIII with guanidine in the presence of an acid in protic solvent such as ethanol. The pyrimidone of Formula IX is then converted to the chloropyrimidine IIb, (II, where $R_3$ is $NH_2$) under typical conditions, e.g., $POCl_3$ and heat.

Reaction Scheme 6

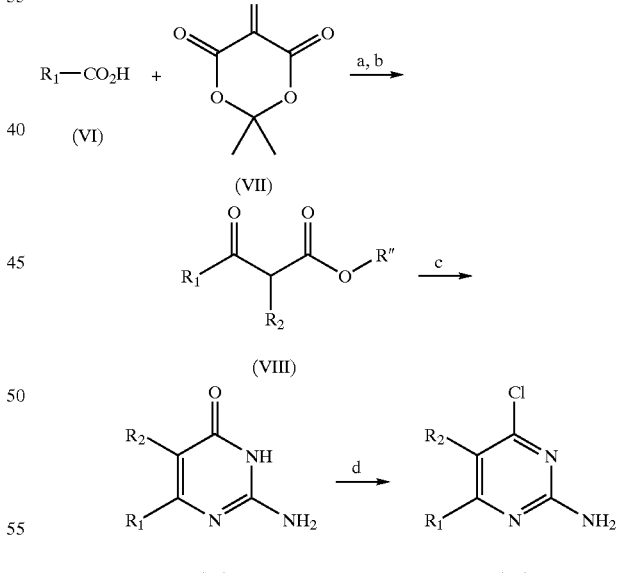

(IX)   (IIb)

R″ = lower alkyl, benzyl
a) DMAP/DCC/$CH_2Cl_2$, 0° C. - rt; b) pTsOH.$H_2O$/R″OH, reflux;
c) Guanidine carbonate, HCl, EtOH, reflux; d) $POCl_3$, 100° C.

Without further elaboration, it is believed that one skilled in the art can, using the preceding descriptions, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius; and, unless otherwise indicated, all parts and percentages are by weight.

The entire disclosure of all applications, patents and publications, cited above or below, and U.S. Provisional Application Ser. No. 60/349,987, filed Jan. 23, 2002, are hereby incorporated by reference.

Abbreviations and Acronyms

When the following abbreviations are used herein, they have the following meaning:

| | |
|---|---|
| Ac₂O | acetic anhydride |
| anhy | anhydrous |
| n-BuOH | n-butanol |
| t-BuOH | t-butanol |
| CD₃OD | methanol-d₄ |
| Celite ® | diatomaceous earth filter agent, ® Celite Corp. |
| CH₂Cl₂ | methylene chloride |
| CI-MS | chemical ionization mass spectroscopy |
| conc | concentrated |
| dec | decomposition |
| DME | dimethoxyethane |
| DMF | N,N-dimethylformamide |
| DMSO | dimethylsulfoxide |
| ELSD | evaporative light scattering detector |
| EtOAc | ethyl acetate |
| EtOH | ethanol (100%) |
| Et₂O | diethyl ether |
| Et₃N | triethylamine |
| HPLC ES-MS | high performance liquid chromatography-electrospray mass spectrometry |
| LC | liquid chromatography |
| MPLC | medium pressure liquid chromatography |
| MS | mass spectrometry |
| NMM | 4-methylmorpholine |
| Ph₃P | triphenylphosphine |
| Pd(dppf)Cl₂ | [1,1'-bis(diphenylphosphino)ferrocene] dichloropalladium(II) |
| Pd(PPh₃)₄ | tetrakis(triphenylphosphine)palladium(0) |
| Pd(OAc)₂ | palladium acetate |
| P(O)Cl₃ | phosphorous oxychloride |
| RT | retention time (HPLC0) |
| rt | room temperature |
| THF | tetrahydrofuran |
| TFA | trifluoroacetic acid |
| TLC | thin layer chromatography |

EXPERIMENTAL EXAMPLES

All reactions were performed in flame-dried or oven-dried glassware under a positive pressure of dry argon, and were stirred magnetically unless otherwise indicated. Sensitive liquids and solutions were transferred via syringe or cannula, and introduced into reaction vessels through rubber septa. Commercial grade reagents and solvents were used without further purification. Thin layer chromatography (TLC) was performed on Analtech UNIPLATE™ pre-coated glass-backed silica gel 60 A F-254 250 μm plates. Column chromatography (flash chromatography) was performed on a Biotage system using 32–63 micron, 60 A, silica gel pre-packed cartridges. Proton ($^1$H) nuclear magnetic resonance (NMR) spectra were measured with a Varian (300 MHz) spectrometer with residual protonated solvent (CHCl₃ δ 7.26; MeOH δ 3.30; DMSO δ 2.49) as standard. Low-resolution mass spectra (MS) were either obtained as electron impact (EI) mass spectra or as fast atom bombardment (FAB) mass spectra.

The IUPAC name was obtained using the ACD/ILab Web service.

A. Preparation of Reparation of Chloropyrimidine Intermediates

Intermediate A1

Preparation of 2-amino-4-chloro-5,6-dimethyl-pyrimidine

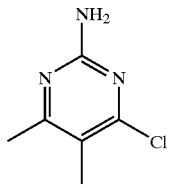

Step 1. Preparation of 2-amino-5,6-dimethyl-4-pyrimidinone

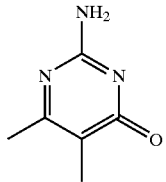

To a solution of ethyl 2-acetoacetate (6.0 g, 41.6 mmol) and guanidine carbonate (5.6 g, 31.2 mmol) in EtOH (32 mL) was added 12 N HCl (350 μL). The mixture was refluxed for 16 h. After the reaction was cooled to room temperature, the solid was collected by filtration and washed with EtOH. A solution of the solid in 1 N NaOH was refluxed for 3 h. After the reaction was cooled to room temperature, the aqueous mixture was adjusted to pH=5 with concentrated acetic acid. The resulting precipitate was collected by filtration, washed with water and then with hexanes, and dried under vacuum. Desired compound (6.34 g, 45.6 mmol; 100% yield); $^1$H NMR (D₂O; NaOD) δ 1.47 (s, 3H), 1.29–1.30 (m, 2H), 1.22 (s, 3H); ES MS [M+H]⁺= 140.

Step 2. Preparation of 2-amino-4-chloro-5,6-dimethyl-pyrimidine

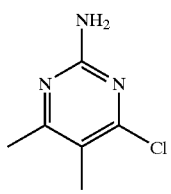

The product of the previous step (2.0 g, 14.4 mmol) and phosphorus oxychloride (6 mL, 57.5 mmol), was refluxed for 4 h. The reaction was cooled to rt and poured over ice. The mixture was separated and the aqueous layer was extracted with chloroform (3×75 mL). The aqueous mixture was adjusted to pH=9 with concentrated ammonium hydroxide. The resulting solid product was collected by filtration, washed with water, and dried under vacuum. Desired compound (963 mg, 6.1 mmol; 43% yield); mp=212–220° C.; ES MS [M+H]⁺=158; TLC (CH₂Cl₂—MeOH, 90:10); R$_f$=0.72.

Intermediate A2

Preparation of 2-amino-4-chloro-6-(4-pyridyl)pyrimidine

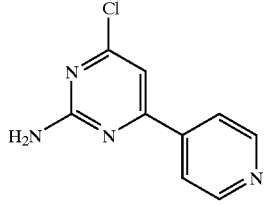

Step 1. Preparation of 2-amino-4-hydroxy-6-(4-pyridyl)pyrimidine

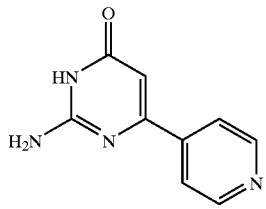

A solution of guanidine carbonate (7.1 g, 39 mmol, 1.5 eq), ethyl isonicotinoyl acetate (10 g, 51.76 mmol), and hydrochloric acid (0.75 mL, 9.0 mmol) in absolute ethanol (80 mL) was refluxed under argon overnight. The precipitate formed was filtered, washed with ethanol and dried. The solid was then dissolved in 1 N NaOH (100 mL) and refluxed for 2 h. The reaction mixture was then cooled to room temperature, acidified with glacial acetic acid, and the solid formed was filtered and dried to afford the desired product as a white solid (5.45 g, 56%). $^1$H-NMR (DMSO-$d_6$) δ 6.24 (s, 1H), 6.79 (bs, 2H), 7.85 (d, J=5.1 Hz, 2H), 8.62 (d, J=5.3 Hz, 2H), 11.22 (bs, 1H).

Step 2. Preparation of 2-amino-4-chloro-6-(4-pyridyl)pyrimidine:

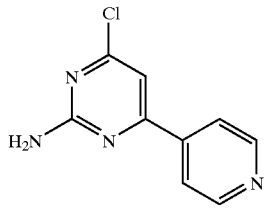

A solution of 2-amino-4-hydroxy-6-(4-pyridyl)pyrimidine (5.45 g, 29 mmol) in POCl$_3$ (12 mL) was refluxed under argon for 5 h. The reaction mixture was cooled to room temperature, poured over ice, and allowed to stir at room temperature for 2 h to ensure the quenching of POCl$_3$. At this time, the mixture was made basic upon addition of 1 N NaOH and the brown solid was filtered to afford 4.52 g of crude product, which was used without further purification (NMR analysis showed 1:1 product/starting material). The filtrate formed more solid upon standing at room temperature (1 g, NMR analysis showed 2:1 product/starting material). $^1$H-NMR (DMSO-$d_6$) δ 7.34 (bs, 2H), 7.38 (s, 1H), 7.99 (d, J=4.2 Hz, 2H), 8.72 (d, J=4.6 Hz, 2H).

Intermediate A3

Preparation of 2-amino-4-chloro-6-(2-thienyl)pyrimidine

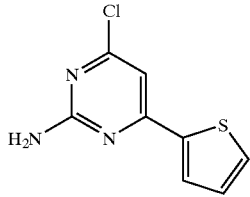

Step 1. Preparation of ethyl-2-(thiophene-2-oyl)acetate.

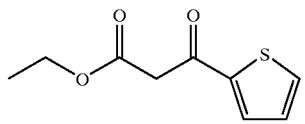

A solution of thiophene-2-carboxylic acid (8.9 g, 68.5 mmol), 2,2-dimethyl-1,3-dioxane-4,6-dione (12.0 g, 81.6 mmol), and 4-dimethylaminopyridine (17.0 g, 138 mmol) in dry CH$_2$Cl$_2$ (100 mL) was cooled to 0° C. and treated with a solution of 1,3-dicyclohexylcarbodiimide (75 mL, 1.0 M in CH$_2$Cl$_2$, 75 mmol). The reaction was allowed to stir at room temperature for 2 h and the dicyclohexylurea was then filtered and washed with CH$_2$Cl$_2$. The filtrate was concentrated at reduced pressure and the residue was dissolved in absolute ethanol (400 mL). The solution was then treated with a solution of p-toluenesulfonic acid monohydate (32 g, 168 mmol) in absolute ethanol (100 mL) and refluxed under argon for 1 h. At this time, the ethanol was removed at reduced pressure and the residue was dissolved in EtOAc and washed sequentially with H$_2$O (300 mL), saturated NaHCO$_3$ (200 mL), 1 N HCl (200 mL), saturated NaCl, and dried (MgSO$_4$). The solvent was removed at reduced pressure and the residue was filtered through a pad of silica with 10% EtOAc/90% hexanes to afford the desired product as an oil (13 g, 96%). TLC (20% EtOAc/80% hexane) R$_f$ 0.21; $^1$H-NMR (DMSO-$d_6$) δ 1.17 (t, J=7.01, 3H), 4.06–4.14 (m, 4H), 7.25 (t, J=5.1 Hz, 1H), 7.98 (d, J=3.8 Hz, 1H), 8.06 (d, J=4.9 Hz, 1H).

Step 2. Preparation of 2-amino-4-hydroxy-6-(2-thienyl)pyrimidine.

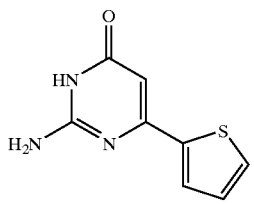

The procedure was similar to that used for Intermediate A2, step 1, using ethyl-2-(thienyl-2-oyl)acetate as starting material. (43% yield). TLC (6% MeOH/94% CH$_2$Cl$_2$) R$_f$ 0.23; MS ES 194 [M+H]$^+$; $^1$H-NMR (DMSO-$d_6$) δ 6.06 (s, 1H), 6.70 (bs, 2H), 7.11 (t, J=4.9 Hz, 1H), 7.64 (d, J=4.9 Hz, 1H), 7.70 (d, J=3.6 Hz, 1H), 10.95 (bs, 1H).

Step 3. Preparation of 2-amino-4-chloro-6-(2-thienyl)pyrimidine.

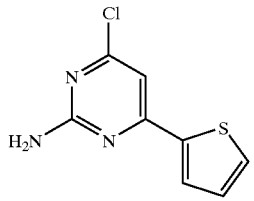

The procedure was similar to that of Intermediate A2, step 2, using 2-amino-4-hydroxy-6-(2-thiophene)pyrimidine as starting material. It afforded 33% yield after purification on silica with 15% EtOAc/85% hexanes. TLC (20% EtOAc/80% hexanes) $R_f$ 0.29; $^1$H-NMR (DMSO-$d_6$) δ 7.16–7.23 (m, 4H), 7.77 (dd, J=0.8, 5.0 Hz, 1H), 7.98 (dd, J=1.0, 3.8 Hz, 1H).

Intermediate A4

Preparation of 2-amino-4-chloro-6-(2-furyl)pyrimidine

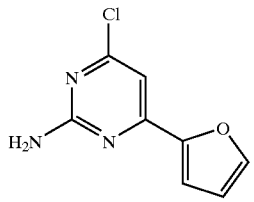

Step 1. Preparation of 2-amino-4-hydroxy-6-(2-furyl)pyrimidine.

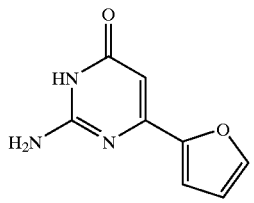

The general procedure for the preparation of Intermediate A2, (step 1) was used; (37% yield). MS (ES) 178 [M+H]$^+$.

Step 2. Preparation of 2-amino-4-chloro-6-(2-furyl)pyrimidine.

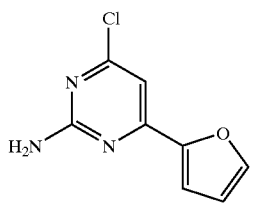

A solution of 2-amino-4-hydroxy-6-(2-furyl)pyrimidine (1.40 g, 7.9 mmol) in POCl$_3$ (4 mL) was refluxed under argon for 2 h. The POCl$_3$ was distilled; the residue was diluted with EtOAc and poured over iced saturated NaHCO$_3$. The layers were separated and the aqueous was extracted with EtOAc (100 mL). The combined extracts was washed with saturated NaCl, dried (MgSO$_4$), and the solvent removed at reduced pressure to afford 0.5 g of crude product, which was used without further purification. TLC (20% EtOAc/80% hexane) $R_f$ 0.26; $^1$H-NMR (DMSO-$d_6$) δ 6.68 (dd, J=1.7, 3.4 Hz, 1H), 6.94 (s, 1H), 7.25 (dd, J=1, 3.7 Hz, 1H), 7.91 (dd, J=0.8, 1.9 Hz, 1H).

Intermediate A5

Preparation of 6-benzyl-4-chloro-5,6,7,8-tetrahydropyrido[4,3-d]pyrimidin-2-amine

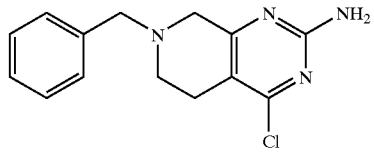

Step 1. Preparation of 2-amino-7-benzyl-5,6,7,8-tetrahydropyrido[3,4-d]pyrimidin-4(3H)-one.

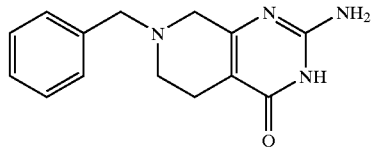

To EtOH (16 mL) cooled to 0° C. (ice/H$_2$O bath) was added Na spheres (204 mg, 8.9 mmol). The mixture was stirred until all Na dissolved. Methyl 1-benzyl-4-oxo-3-piperidine-carboxylate hydrochloride (3.0 g, 10.1 mmol) and guanidine carbonate (1.4 g, 7.6 mmol) were added. The mixture was refluxed for 16 h. After the reaction was cooled to room temperature, the solid was collected by filtration, washed with EtOH, and dried under vacuum. Desired compound (2.58 g, 10.0 mmol; 99+% yield); mp=202–212° (dec.); ES MS [M+H]$^+$=257; TLC (CH$_2$Cl$_2$—MeOH, 90:10); $R_f$=0.20.

Step 2. Preparation of 6-benzyl-4-chloro-5,6,7,8-tetrahydropyrido[4,3-d]pyrimidin-2-amine.

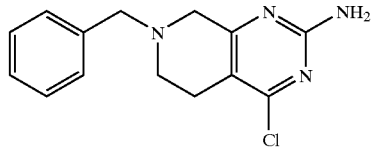

A solution of the product from step 1 (3.5 g, 13.7 mmol) in POCl$_3$ (52 mL) was refluxed under argon for 5 h. The reaction mixture was cooled to room temperature, poured over ice, and allowed to stir at room temperature for 2 h to ensure the quenching of POCl$_3$. At this time, the mixture was made basic upon addition of ammonium hydroxide and was extracted with CH$_2$Cl$_2$ (3×200 mL). The combined organics were washed with 1N NaOH followed by brine, dried (MgSO$_4$), and concentrated under reduced pressure. The residue was taken up in benzene and was made acidic upon the addition of 1N HCl in diethyl ether. The brown solid was filtered to afford 0.35 g of crude product, which was used without further purification. ES MS [M+H]$^+$=275.

Intermediate A6

Preparation of 2-amino-6-(trifluoromethyl)-4-pyrimidinyl 4-methylbenzenesulfonate

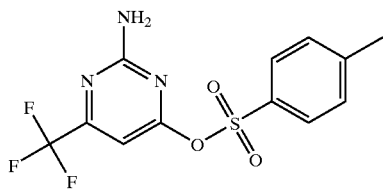

To a solution of 2-amino-6-(trifluoromethyl)-4(3H)-pyrimidinone (250 mg, 1.4 mmol), triethylamine (196 μL, 1.4 mmol), N,N-dimethylaminopyridine (17 mg, 0.14 mmol), in $CH_2Cl_2$ (13 mL) cooled to 0° C. was added p-toluenesulfonyl chloride (534 mg, 2.8 mmol). The mixture was stirred at room temperature for 16 h. The mixture was diluted with $CH_2Cl_2$, washed with $H_2O$ (2×20 mL) followed by brine, dried ($Na_2SO_4$), evaporated, and dried under vacuum. Desired compound (466 mg, 1.4 mmol; 99+% yield; ES MS $[M+H]^+$=140.

Using the above methods for the preparation of A1–A6 and substituting the appropriate starting materials, the following pyrimidine intermediates were also prepared.

TABLE 1

Chloropyrimidine Intermediates A

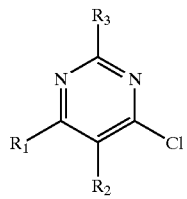

| Intermediate No. | $R_1$ | $R_2$ | $R_3$ | Physical Data |
|---|---|---|---|---|
| A7 | Me | H | $NH_2$ | Aldrich |
| A8 | Et | H | $NH_2$ | Aldrich or Lancaster |
| A9 | H | H | $NH_2$ | Aldrich |
| A10 | t-Bu | H | $NH_2$ | mp = 109–113° C.; ES MS $[M + ]^+$ = 186; TLC(90:10 $CH_2Cl_2$/MeOH); $R_f$ = 0.37. |
| A11 | Me | Cl | $NH_2$ | Aldrich or Lancaster? |
| A12 | —(CH)$_4$— | | $NH_2$ | $^1$H NMR(DMSO-$d_6$)δ6.60(s, 2H), 2.55–2.29(m, 4H), 1.68–1.56(m, 4H) |
| A13 | —(CH)$_5$— | | $NH_2$ | $^1$H NMR(DMSO-$d_6$)δ6.65(s, 2H), 2.72–2.58(m, 4H), 1.74–1.60 (m, 2H), 1.55–1.34(m, 4H) |
| A14 | —(CH)$_3$— | | $NH_2$ | $^1$H NMR(DMSO-$d_6$)δ6.73(s, 2H), 2.72–2.57 (m, 4H), 1.89 (sept, J=7.0, 2H) |
| A15 | i-Pr | H | $NH_2$ | mp = 104–112° C.; $^1$H NMR($D_2O$) δ6.11(s, 1H), 2.23–2.11(m, 1H), 0.46(d, J=6.2Hz, 6H); ES MS $[M + H]^+$ = 172 |
| A16 | $CH_3$ | H | Ph—NH— | |
| A17 | Ph | H | $NH_2$ | |
| A18 | 3-pyridyl | H | $NH_2$ | |
| A19 | 2-pyridyl | H | $NH_2$ | |

TABLE 1-continued

Chloropyrimidine Intermediates A

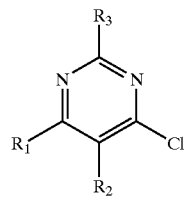

| Intermediate No. | $R_1$ | $R_2$ | $R_3$ | Physical Data |
|---|---|---|---|---|
| A20 | 3-$NO_2$—Ph | H | $NH_2$ | |
| A21 | Cl | H | $NH_2$ | Aldrich |

B. PREPARATION OF ARYLAMINE INTERMEDIATES

Intermediate B1

Preparation of 1-(4-pyridinyl)-1H-indol-5-amine

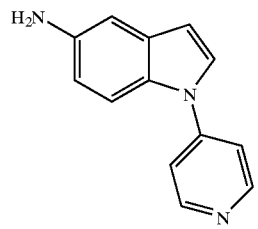

Step 1. Preparation of 5-nitro-1-(4-pyridinyl)-1H-indole

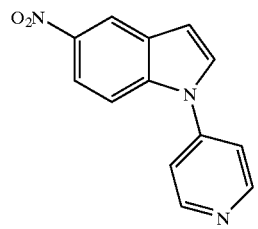

To a solution of 5-nitroindole (7.0 g, 43.2 mmol) and 4-chloropyridine hydrochloride (7.8 g, 51.8 mmol) in DMF (43 mL) was added potassium tert-butoxide (12.1 g, 108.0 mmol), portionwise. The reaction was heated at 100° C. for 48 h. The mixture was allowed to cool to room temperature and poured into water (400 mL). The resulting solid was removed by filtration and dried under vacuum. Desired compound (6.04 g, 25.3 mmol; 58% yield); $^1$H NMR (DMSO-$d_6$) δ 8.76 (dd, J=1.7, 4.5, 2H), 8.68 (d, J=2.2, 1H), 8.06–8.13 (m, 2H), 7.92 (d, J=9.2, 1H), 7.75 (dd, J=1.5, 4.6, 2H), 7.07 (dd, J=0.9, 3.5, 1H); ES MS $[M+H]^+$=240.

Step 2. Preparation of 1-(4-pyridinyl)-1H-indol-5-amine

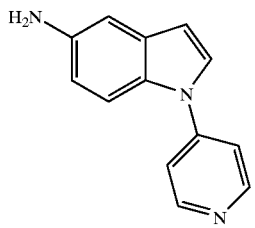

A mixture of the product from step 1 (8.27 g, 34.6 mmol) and 10% palladium-on-charcoal catalyst (827 mg) in ethyl acetate (166 mL) and EtOH (9 mL) was stirred under hydrogen at atmospheric pressure for 48 h. Further catalyst (414 mg) was added and the reaction was stirred for 24 h. Again, further catalyst (414 mg) was added and the reaction was stirred an additional 24 h. The catalyst was removed by filtration through diatomaceous earth and the solvent removed from the filtrate by evaporation. The residue was triturated with ether, collected by filtration, and dried under vacuum. Desired compound (4.67 g, 22.3 mmol; 65% yield); mp=149–154° C.; ES MS $[M+H]^+$=210; TLC ($CH_2Cl_2$—MeOH, 95:5); $R_f$=0.29.

Intermediate B2

Preparation of 4-[(4-aminophenyl)sulfanyl]phenol

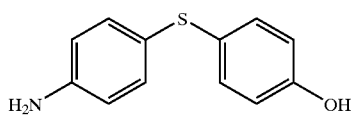

Step 1. Preparation of 4-[(4-nitrophenyl)sulfanyl]phenol.

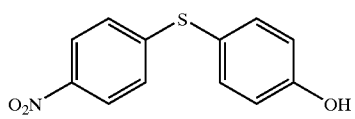

To a solution of nitrobenzenesulfonyl chloride (4 g, 21 mmol) in ether (25 mL) was added phenol (1.97 g, 20 mmol) as a solution in ether (25 mL). After being stirred for 15 h at rt, the mixture was concentrated to afford a crude solid which was recrystallized from acetic acid. Desired compound (4.0 g, 16.2 mmol, 76% yield). TLC (Hexanes/EtOAc, 70:30); $R_f$=0.54.

Step 2. Preparation of 4-[(4-aminophenyl)sulfanyl]phenol.

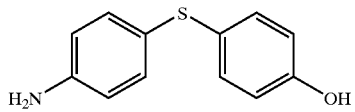

To a solution of the product of step 1 (4 g, 16.2 mmol) in EtOH (500 mL) was added $SnCl_2.2H_2O$ (18.3 g, 81 mmol) The solution was warmed to reflux. After being stirred for 3 h, the mixture was allowed to cool to rt, and the volatiles were removed by rotary evaporation. The resultant slurry was suspended in EtOAc, and solid $NaHCO_3$ was added. Subsequently, the mixture was filtered, and the filtered solid was washed thoroughly with EtOAc. The organic filtrate was washed with water, and the aqueous washes were extracted with EtOAc. The combined organic extracts were washed with brine, dried ($MgSO_4$), filtered, and concentrated to afford an orange solid, which was used without additional purification. Desired compound (3.0 g, 13.8 mmol, 86% yield). TLC (Hexanes/EtOAc, 70:30); $R_f$=0.34.

Intermediate B3

Preparation of (3-aminophenyl)[4-(methylsulfanyl)phenyl]methanone

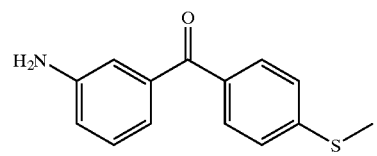

Step 1. Preparation of [4-(methylsulfanyl)phenyl](3-nitrophenyl)methanone

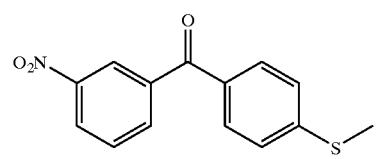

3-nitrobenzoylchloride (5.0 g, 26.94 mmol) was added to a solution of thioanisole (3.16 mL, 26.94 mmol) and 1,2-dichlorethane (95 mL). The resulting reaction mixture was cooled to 0° C. (ice/$H_2O$ bath) and 0.5 equivalents of aluminum trichloride (1.8 g, 13.47 mmol) was added. The reaction was allowed to stir for 15 min at this temperature and the cold bath was removed followed by addition of the remaining equivalents of $AlCl_3$ (2.51 g, 18.87). The reaction solution turned a dark greenish/yellow and was allowed to stir at room temp. for 18 h, after which time the reaction was quenched slowly with $H_2O$ (50 mL). The mixture was diluted with $CH_2Cl_2$ (50 mL) and washed with $H_2O$ (3×50 mL), and the combined organic phases were washed with satd $NaHCO_3$ (50 mL), dried ($MgSO_4$) and concentrated under reduced pressure. The crude material was purified by silica gel column chromatography (EtOAc/hexane, 1/4) to afford 3.3 g (44%) of 4-(methylsulfanyl)phenyl](3-nitrophenyl)methanone as a solid. EI-LRMS m/z 274 ($M^+$); TLC Rf0.68 (EtOAc/Hex, 2/3).

Step 2. Preparation of (3-aminophenyl)[4-(methylsulfanyl)phenyl]methanone

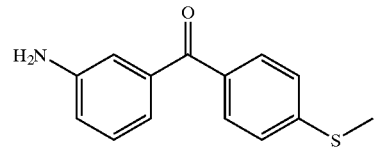

Prepared analogously to Intermediate B2, step 2. The crude product was purified by flash column chromatography, eluting with 70:30 Hexanes/EtOAc. TLC: (Hexanes/EtOAc, 70:30); $R_f$=0.15.

Intermediate B4

Preparation of 4-(4-aminophenoxy)phenol

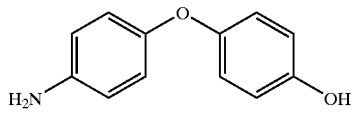

Step 1. Preparation of 4-(4-nitrophenoxy)phenol

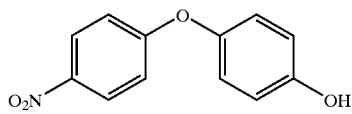

A mixture of p-nitrofluorobenzene (25 g, 0.177 mol), dihydroquinone (19.5 g, 0.177 mol), and sodium hydroxide (7.08 g, 0.177 mol) in EtOH/H2O (1:1 v/v, 176 mL) was heated at reflux for 20 h, and subsequently allowed to cool to room temperature. The mixture was filtered, the filtrate was made acidic with dilute aqueous HCl, and the resultant precipitate filtered to afford the crude product as a yellow solid. The desired product was recrystallized from EtOH. (15 g, 0.064 mol, 37% yield). TLC (Hexanes/EtOAc, 70:30); $R_f$=0.44.

Step 2. Preparation of 4-(4-aminophenoxy)phenol

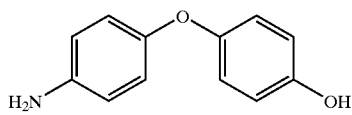

To a solution of the product of step 1 in EtOH (100 mL) was added 10% palladium on carbon (200 mg). After being stirred under an atmosphere of hydrogen overnight, the mixture was filtered through Celite®. The volatiles were removed from the filtrate to provide the crude product which was purified by flash column chromatography eluting with Hexanes/EtOAc (85:15, followed by 75:25). Desired product (1.5 g, 7.45 mmol, 86%). TLC (Hexanes/EtOAc, 70:30); $R_f$=0.41.

Intermediate B5

Preparation of 4-(4-pyridinylthio)aniline

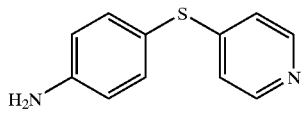

To a solution of 4-aminothiophenol (20.2 g, 156.5 mmol) in anhydrous DMF (200 mL) was added 4-chloropyridine hydrochloride (24.4 g, 161.0 mmol) followed by potassium carbonate (44 g, 318.4 mmol). The reaction mixture was heated at 80° C. overnight, then diluted with ethyl acetate (400 mL) and water (400 mL). The aqueous layer was back-extracted with ethyl acetate (2×200 mL). The combined organic layers were washed with a saturated aqueous NaCl solution (200 mL), dried over anhy $MgSO_4$, and concentrated under reduced pressure. The residue was filtered through a pad of silica with ethyl acetate and the resulting material was triturated with an ethyl ether/hexane solution to afford the desired product (24.7 g, 78%). TLC (50% ethyl acetate/50% hexane) $R_f$=0.25; $^1$H-NMR (DMSO-$d_6$) δ 5.67 (bs, 2H), 6.65 (d, J=8.4 Hz, 2H), 6.88 (d, J=6.2 Hz, 2H), 7.19 (d, J=8.4 Hz, 2H), 8.27 (d, J=6.2 Hz, 2H), MS[M+H]$^+$=203.

Intermediate B6

Preparation of 4-[2-(4-pyridinyl)ethyl]aniline

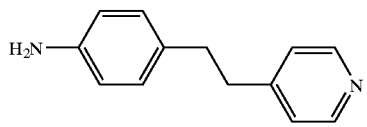

Step 1. Preparation of 4-[(E)-2-(4-nitrophenyl)ethenyl]pyridine

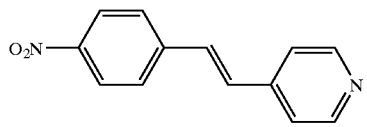

To an oven dried 500 mL 3-necked flask was added (4-nitrobenzyl)triphenylphosphonium bromide (15 g, 30.42 mmol) followed by the addition of THF (100 mL). The solution was cooled to 0° C. in an ice bath. Potassium t-butoxide (3.9 g, 33.02 mmol) was then added in one portion resulting in an orange suspension. The suspension was maintained at 0° C. while a solution of 4-pyridine-2-carboxaldehyde (2.7 g, 24.70 mmol) in THF (20 mL) was added in 10 minutes. The ice bath was removed and the reaction was stirred at room temperature for 2 h. At this time, the reaction was quenched with saturated ammonium chloride solution (50 mL) and stirred for 15 minutes. The mixture was then extracted with ethyl acetate (2×100 mL), the combined extracts was washed with saturated aqueous NaCl solution (100 mL) and dried (MgSO$_4$). The solvent was removed at reduced pressure and the residue was chromatographed on silica with 0–50% ethyl acetate in hexanes to afford the desired product (1.8 g, 32%). TLC (50% ethyl acetate/50% hexane) $R_f$=0.28; $^1$H-NMR (DMSO-$d_6$) δ 6.84 (d, J=12.4 Hz, 1H), 6.96 (d, J=12.4 Hz, 1H), 7.14 (d, J=6.2 Hz, 2H), 7.45 (d, J=8.7 Hz, 2H), 8.15 (d, J=8.7 Hz, 2H), 8.47 (d, J=6.2 Hz, 2H).

Step 2. Preparation of 4-[2-(4-pyridinyl)ethyl]aniline

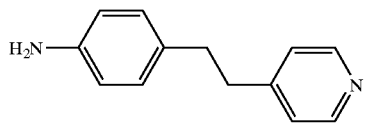

To a dry 50 mL flask flushed with argon was added 10% Pd on carbon (285 mg) followed by the addition of ethanol (12 mL) and the product from step 1 (1.8 g, 8.0 mmol). At this time, the argon line was replaced with a hydrogen balloon and the reaction was stirred overnight. The mixture was filtered through a pad of Celite® and the filtrate was concentrated at reduced pressure. The solid residue was triturated with ethyl ether/hexanes to afford the desired product (1.2 g, 67%). TLC (4% acetone/96% methylene chloride) $R_f$=0.09; $^1$H-NMR (DMSO-$d_6$) δ 2.67–2.83 (m, 4H), 4.83 (bs, 2H), 6.45 (d, J=8.2 Hz, 2H), 6.84 (d, J=8.2 Hz, 2H), 7.20 (d, J=6 Hz, 2H), 8.41 (d, J=6 Hz, 2H).

Intermediate B7

Preparation of 3-fluoro-4-(4-pyridinylsulfanyl)aniline

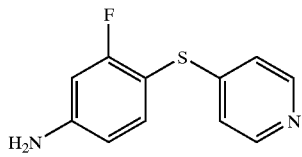

Step 1. Preparation of 4-[(2-fluoro-4-nitrophenyl)sulfanyl]pyridine.

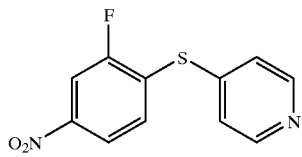

A solution of 4-mercaptopyridine (4.2 g, 35.6 mmol), 3,4-difluoronitrobenzene (5.7 g, 35.7 mmol), and potassium carbonate (12.4 g, 89.7 mmol) in anhydrous DMF (40 mL) was stirred at 40° C. and under argon for 3 h. TLC showed complete reaction. The mixture was diluted with ethyl acetate (100 mL) and water (100 mL) and the aqueous layer was back-extracted with ethylacetate (2×100 mL). The organic layers were washed with a saturated NaCl solution (100 mL), dried (MgSO$_4$), and concentrated under reduced pressure. The crude product was purified by column chromatography with 50% ethyl acetate/50% hexanes. It afforded the desired product as a yellow solid (6.3 g, 71%). TLC (50% EtOAc/50% hexane) R$_f$ 0.53; $^1$H-NMR (DMSO-d$_6$) δ 7.27 (dd, J=0.76, 4.2 Hz, 2H), 7.78 (dt, J=0.76, 7.2 Hz, 1H), 8.11–8.15 (m, 1H), 8.28–8.33 (m, 1H), 8.5 (dd, J=1.4, 4.6 Hz, 2H), MS [M+H]$^+$=251.

Step 2. Preparation of 3-fluoro-4-(4-pyridinylsulfanyl)aniline.

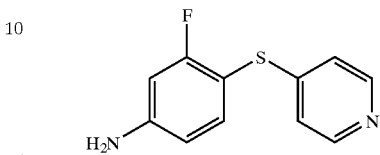

A slurry of 3-fluoro-4-pyridinylthio)nitrobenzene (6.3 g, 25.2 mmol), iron powder (6.0 g, 107.4 mmol), acetic acid (100 mL), and water (1 mL) were stirred at room temperature overnight. The mixture was diluted with Et$_2$O (100 mL) and water (100 mL). The aqueous phase was adjusted to pH 5 with a 4 N NaOH solution. The combined organic layers were washed with an aqueous saturated NaCl solution (100 mL), dried (MgSO$_4$), and concentrated under reduced pressure. The residue was purified by column chromatography with 50% ethyl acetate/50% hexanes. It afforded the desired product as a white solid (4.8 g, 86%). TLC (50% EtOAc/50% hexane) R$_f$=0.28; $^1$H-NMR (DMSO-d$_6$) δ 6.04 (bs, 2H), 6.47–6.51 (m, 2H), 6.91 (d, J=6.1 Hz, 2H), 7.22 (t, J=8.4 Hz, 1H), 8.30 (d, J=6.4 Hz, 2H).

Using similar methods to those described for the preparation of Intermediates B1–B7, the following additional compounds were also prepared:

TABLE 2

Acrylamine Intermediates B

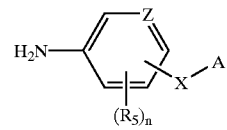

| Intermediate No. | Z | (R$_5$)$_n$ | —X— | A | Physical Properties |
|---|---|---|---|---|---|
| B8 | CH | H | (4)-S—CH$_2$— | pyrid-4-yl | TLC Rf = 0.12(50% EtOAc/50% hexanes). 1H NMR(DMSO-d6)δ3.91(s, 2H), 5.26(bs, 2H), 6.44(d, J=8.7Hz, 2H), 6.96(d, J=8.7 Hz, 2H), 7.12(d, J=6.3Hz, 2H), 8.40(d, J=6.0Hz, 2H). |
| B9 | CH | 3-CF$_3$ | (4)-S— | pyrid-4-yl | TLC Rf = 0.10(50% EtOAc/50% hexanes). 1H NMR(DMSO-d6)δ6.21(bs, 2H), 6.84–6.87 (m, 3H), 7.10(d, J=2.4Hz; 1H), 7.39 (d, J=8.4Hz, 1H), 8.29(d, J=6.3Hz, 2H). |
| B10 | CH | H | (4)-O— | isoquinolin-5-yl | |
| B11 | CH | 3-F | (4)-O— | isoquinolin-5-yl | 1H NMR(DMSO-d6)δ5.42(bs, 2H), 6.41–6.55 (m, 2H), 6.81–7.05(m, 2H), 7.48–7.54 (m, 1H), 7.73–7.76(m, 1H), 8.06–8.08(m, 1H), 8.54–8.56(m, 1H), 9.32(s, 1H). |
| B12 | CH | 3,5-(Cl)$_2$ | (4)-O— | isoquinolin-5-yl | TLC Rf = 0.29(45% EtOAc/55% hexanes). 1H NMR(DMSO-d6)δ5.73(bs, 2H), 6.69 (dd, J=1.1 and 8.0Hz, 1H), 6.75(s, 2H), 7.51(t, J=7.7Hz, 1H), 7.78(d, J=8.2Hz, 1H), 8.12(d, J=5.9Hz, 1H), 8.58(d, J=5.6 Hz, 1H), 9.34(bs, 1H). |
| B13 | CH | H | (4)-S— | pyrid-4-yl | TLC Rf = 0.07(100% EtOAc). 1H NMR (DMSO-d6)δ5.84(bs, 2H), 6.95–6.99(m, 3H), 7.32(d, J=8.6Hz, 1H), 8.00(d, J=2.8 Hz, 1H), 8.31(d, J=4.7Hz, 2H). |

TABLE 2-continued

Acrylamine Intermediates B

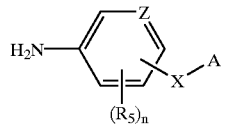

| Intermediate No. | Z | (R$_5$)$_n$ | —X— | A | Physical Properties |
|---|---|---|---|---|---|
| B14 | CH | 3,5-(Cl)$_2$ | (4)-S— | pyrid-4-yl | 1H NMR(DMSO-d6)δ6.30(bs, 2H), 6.82(s, 2H), 6.89, (d, J=6.0Hz, 2H), 8.33(d, J=6.1 Hz, 2H). |
| B15 | CH | 2,5-(F)$_2$ | (4)-S— | pyrid-4-yl | |
| B16 | CH | 3-Cl | (4)-S— | pyrid-4-yl | |
| B17 | CH | H | (4)-S— | isoquinolin-5-yl | |
| B18 | CH | H | (4)-CH$_2$—S— | pyrid-4-yl | |
| B19 | CH | H | (4)-S— | pyrid-3-yl | |
| B20 | CH | H | (3)-S— | pyrid-4-yl | |
| B21 | CH | H | (4)-O— | quinolin-5-yl | |

Intermediate C1

1-Chloro-2,3-difluoro-5-nitrobenzene

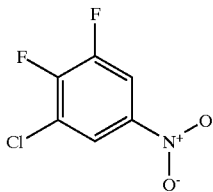

The compound can be obtained by oxidizing 3-chloro-4,5-difluoroaniline, described in JP 05059067, with hydrogen peroxide in trifluoroacetic acid according to a process described in Heaton, A. et al., J. Fluorine Chem. 1997, 81 (2), 133–138 and Krapcho, A. P. et al., J. Org. Chem. 1990, 55 (21), 5662–5664 for the preparation of analogous derivatives.

Intermediate C2

4-[(2-Fluoro-4-nitrophenyl)sulphanyl]pyridine

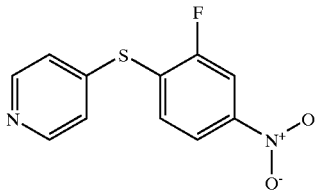

21 g (188.9 mmol) of 4-mercaptopyridine, 30.05 g (188.9 mmol) of 3,4-difluoro-nitrobenzene and 60.05 g (434.5 mmol) of potassium carbonate are dissolved in dimethylformamide, and the mixture is stirred at 40° C. for 3 hours. The reaction solution is then diluted with 500 mL of ethyl acetate and 300 mL of water. The aqueous phase is extracted five times with in each case 100 mL of ethyl acetate. The combined organic phases are washed with 200 mL of saturated sodium chloride solution, dried over sodium sulphate and concentrated under reduced pressure using a rotary evaporator. The residue is purified by MPLC (mobile phase: ethyl acetate:cyclohexane 1:1).

This gives 37.3 g (79% of theory) of product.

$^1$H-NMR (300 MHz, DMSO-d$_6$): δ=7.28 (dd, 2H), 7.79 (t, 1H), 8.15 (dd, 1H), 8.30 (dd, 1H), 8.50 (dd, 2H) LC-MS (method 4): RT=2.68 min MS (ESIpos): m/z=251 (M+H)$^+$ Intermediate C3 below can be prepared from the appropriate mercapto or hydroxy heterocycles and their corresponding 4-fluoro- and 4-chloronitrobenzene derivatives, analogously to the procedure described for C2.

| C3 | 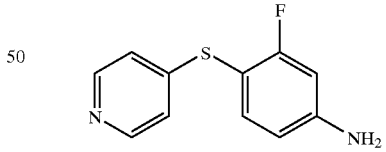 | $^1$H-NMR(300MHz, DMSO-d$_6$): δ=7.15(dd, 2H), 8.37(dd, 1H), 8.41–8.45(m, 3H) HPLC(method 1): RT = 3.77 min MS(CIpos): m/s = 302(M + NH$_4$)$^+$ |
|---|---|---|

Intermediate C4

3-Fluoro-4-(4-pyridinylsulphanyl)aniline 37 g (147.9 mmol) of C2 are dissolved in 1000 mL of ethanol, and 143.86 mL (2.95 mol) of hydrazine hydrate and 4 g of palladium on carbon are added. The reaction mixture is stirred under reflux overnight. After cooling, the mixture is filtered off with suction through silica gel, and the filter cake is washed with ethanol. The filtrate is concentrated under reduced pressure using a rotary evaporator. The residue is suspended in diethyl ether and filtered off with suction. The precipitate is then suspended in water and filtered off with suction. The product is washed two more times with a little water. Drying under high vacuum gives 27.3 g (84% of theory) of product.

¹H-NMR (300 MHz, DMSO-d₆): δ=6.02 (br.s, 2H), 6.49–6.54 (m, 2H), 6.93 (dd, 2H), 7.23 (t, 1H), 8.32 (dd, 2H) LC-MS (method 4): RT 0.96 min MS (ESIpos): m/z=221 (M+H)⁺

Intermediate C5 can be prepared analogously to the procedure described for C4 from the appropriate starting materials.

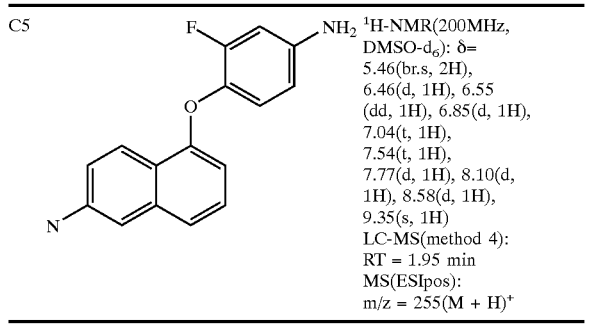

C5 ¹H-NMR(200MHz, DMSO-d₆): δ= 5.46(br.s, 2H), 6.46(d, 1H), 6.55 (dd, 1H), 6.85(d, 1H), 7.04(t, 1H), 7.54(t, 1H), 7.77(d, 1H), 8.10(d, 1H), 8.58(d, 1H), 9.35(s, 1H) LC-MS(method 4): RT = 1.95 min MS(ESIpos): m/z = 255(M + H)⁺

Intermediate C6

3-Chloro-5-fluoro-4-(4-pyridinylsulphanyl)aniline

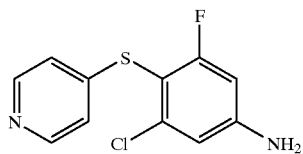

3.19 g (11.205 mmol) of C3 are dissolved in 200 mL of ethanol. 638 mg (2.81 mmol) of platinum(IV) oxide are then added, and the mixture is stirred at RT and atmospheric pressure under an atmosphere of hydrogen for 2 hours. For work-up, the reaction solution is filtered off with suction through kieselguhr and washed thoroughly with ethanol. The filtrate is concentrated under reduced pressure.

This gives 2.755 g (81% of theory) of product.

¹H-NMR (200 MHz, DMSO-d₆): δ=6.37 (s, 2H), 6.49 (dd, 1H), 6.72–6.74 (m, 1H), 6.93 (dd, 2H), 8.34 (dd, 2H) HPLC (method 1): RT=3.68 min MS (ESIpos): m/z=255 (M+H)⁺

Intermediate C7

3,5-difluoro-4-(4-pyridinylsulfanyl)aniline

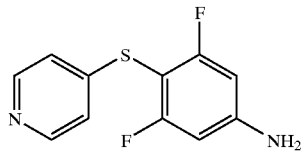

is synthesized analogously to C6 from 4-[(2,6-difluoro-4-nitrophenyl)sulfanyl]pyridine by catalytic reduction with hydrogen on Platin(IV)oxide.

¹H-NMR (300 MHz, DMSO-d₆): δ=6.38 (br. s, 2H), 6.40 (m, 2H), 6.98 (dd, 2H), 8.35 (dd, 2H) HPLC (method 1): RT=3.56 min 4-[(2,6-difluoro-4-nitrophenyl)sulfanyl]pyridine

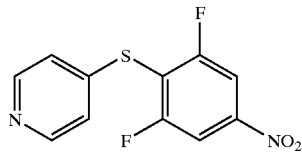

is synthesized analogously to C2 from 4-mercaptopyridine and 1,2,3-trifluoro-5-nitrobenzene.

¹H-NMR (200 MHz, DMSO-d₆): δ=7.22 (dd, 2H), 8.32 (mc, 2H), 8.44 (dd, 2H) HPLC (method 1): RT=3.64 min 1,2,3-trifluoro-5-nitrobenzene

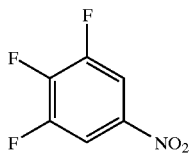

is synthesized analogously to C1 from 3,4,5-trifluoraniline by oxidation with hydrogenperoxide in trifluoroacetic acid.

GC-MS (method 13): RT=3.15 min MS (ESIpos): m/z= 177 (M⁺)

Intermediate C8

3-chloro-4-(4-pyridinylsulfanyl)aniline

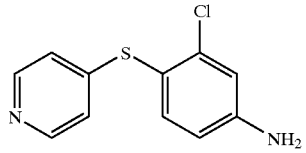

is synthesized analogously to C6 from 4-[(2-chloro-4-nitrophenyl)sulfanyl]pyridine by catalytic reduction with hydrogen on Platin(IV)oxide.

LC-MS (method 7): RT=2.70 min MS (ESIpos): m/z=237 (M+H)⁺

4-[(2-chloro-4-nitrophenyl)sulfanyl]pyridine

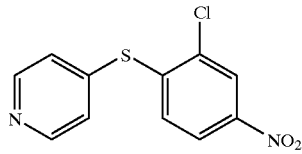

is synthesized analogously to C2 from 4-mercaptopyridine and 1,2-dichloro-4-nitrobenzene.

¹H-NMR (200 MHz, DMSO-d₆): δ=7.42 (dd (2H), 7.55 (d, 1H), 8.19 (dd (1H), 8.47 (d, 1H), 8.50 (dd, 2H) HPLC (method 1): RT=3.72 min HPLC, LCMS and GCMS Methods:

Method 1 (HPLC):

Instrument: HP 1100 with DAD detection; column: Kromasil RP-18, 60 mm×2 mm, 3.5 µm; mobile phase: A=5 mL of HClO₄/l of H₂O, B=acetonitrile; gradient: 0 min 2% B, 0.5 min 2% B, 4.5 min 90% B, 6.5 min 90% B; flow rate: 0.75 mL/min; temp.: 30° C.; detection UV 210 nm.

Method 7 (LCMS):

Instrument: Micromass Platform LCZ, HP1100; column: Symmetry C18, 50 mm×2.1 mm, 3.5 µm; mobile phase A: water+0.05% formic acid, mobile phase B: acetonitrile+0.05% formic acid; gradient: 0.0 min 90% A→4.0 min 10% A→6.0 min 10% A; oven: 40° C.; flow rate: 0.5 mL/min; UV detection: 208–400 nm.

Method 10 (LCMS):

Instrument: Waters Alliance 2790 LC; column: Symmetry C18, 50 mm×2.1, 3.5 µm; mobile phase A: water+0.1% formic acid, mobile phase B: acetonitrile+0.1% formic acid; gradient: 0.0 min 5% B→5.0 min 10% B→6.0 min 10% B; temperature: 50° C.; flow rate: 1.0 mL/min; UV detection: 210 nm.

Method 12 (LCMS):

Instrument: Micromass Platform LCZ, HP 1100; column: Grom-SIL120 ODS-4 HE, 50 mm×2.0 mm, 3 µm; mobile phase A: 1l water+1 mL 50% formic acid, mobile phase B: 1l acetonitrile+1 mL 50% formic acid; gradient: 0.0 min 100% A→0.2 min 100% A→2.9 min 30% A→3.1 min 10% A→4.5 min 10% A; temperature: 55° C.; flow rate: 0.8 mL/min; UV detection: 208–400 nm Method 13 (GCMS):

Instrument: Micromass GCT, GC6890; column: Restek RTX-35MS, 30 m×250 µm×0.25 µm; carrier gas: helium; flow rate: 0.88 mL/min; initial temperature: 60° C.; front injector temp.: 250° C.; gradient: 60° C. (1 min const.), 16° C./min up to 300° C. then 1 min const. 300° C.

The following additional compounds may be produced analogously to the relevant examples above with the (+) and (−) enantiomers being separated on a chiral column:

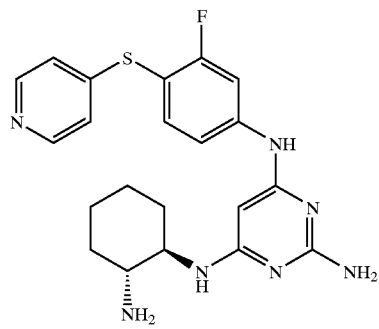

anti isomer, racemic mixture

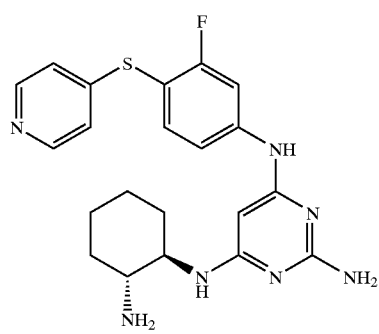

anti isomer, enantiomer 1

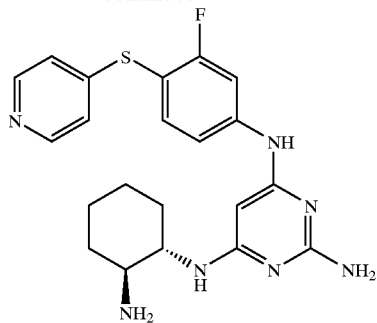

anti isomer, enantiomer 2

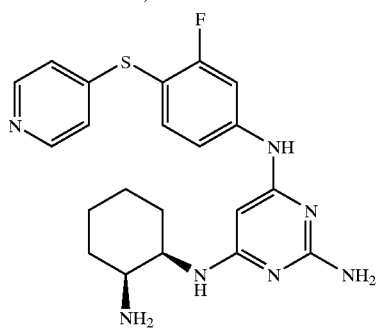

anti isomer, racemic (+) and (−) enantiomers of the above compound may be separated on a chiral column.

D. PREPARATION OF EXAMPLES OF THE INVENTION

Example 1

Preparation of 4-({4-[(2-amino-6-ethyl-4-pyrimidinyl)amino]phenyl}sulfanyl)phenol

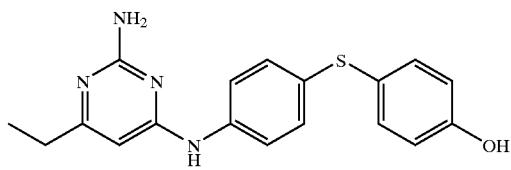

2-Amino-4-chloro-6-ethylpyrimidine (A8, 50 mg, 0.23 mmol) and Intermediate B2(40 mg, 0.25 mmol) were suspended in a mixture of 0.01 M aqueous HCl (230 µL) and 1-butanol (230 µL). The mixture was refluxed overnight. The reaction was cooled to room temperature and quenched with NaHCO$_3$ (satd eq). The precipitated solid was filtered and subsequently purified by reversed phase chromatography on a YMC Pack-pro C18 column (trademark) eluting with acetonitrile/H$_2$O (10:90–90:10 gradient). Desired compound (40.5 mg, 0.11 mmol, 51% yield); mp=181–184° C., TLC (95:5 CH$_2$Cl$_2$/MeOH); R$_f$=0.13

Examples 2–14

Using the above procedures, the following examples of pyridines were synthesized and are summarized in Table 3.

TABLE 3

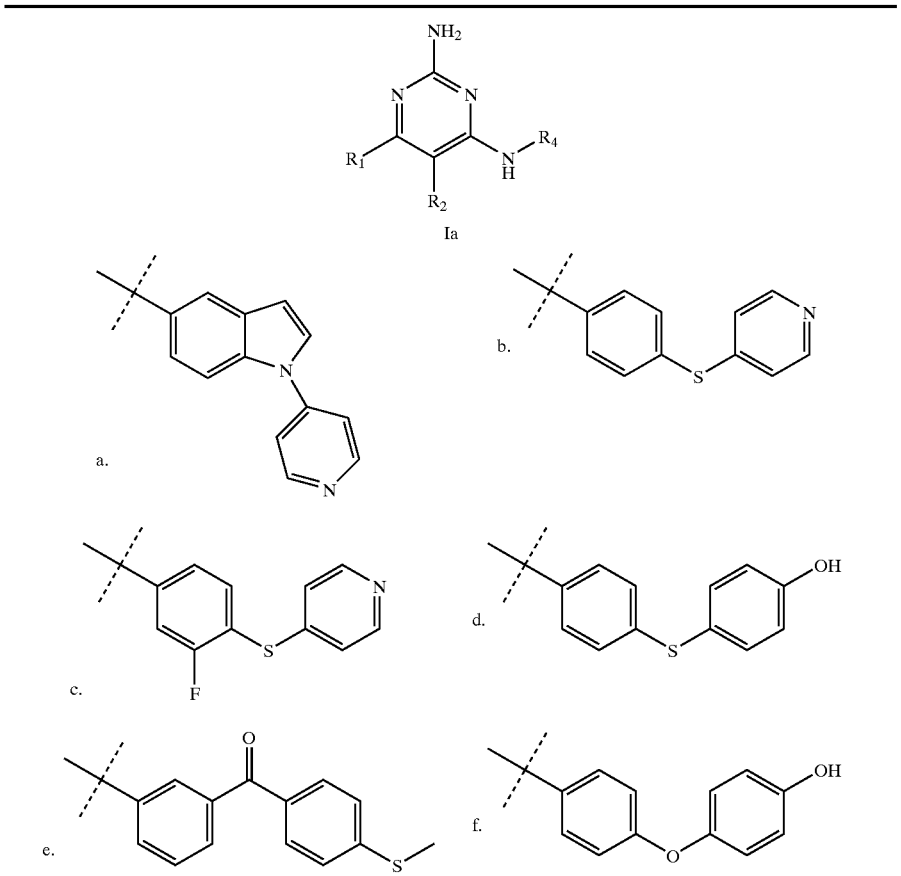

| Ex. No. | Intermediate Pyrimidone (A) | Intermediate Amine (B) | R₁ | R₂ | R₄ | Analytical Data |
|---|---|---|---|---|---|---|
| 2 | A1 | B1 | (CH₃)₃C— | H | a | ¹H NMR(DMSO-d₆)δ11.75(s, 1H), 10.59(s, 1H), 8.78(d, J=5.4, 2H), 8.21(s, 1H), 7.87–7.97 (m, 5H), 7.47(d, J=8.1, 1H), 6.85(d, J= 3.4, 1H), 6.21(s, 1H), 1.29(s, 9H); ES MS [M + H]⁺ = 359. |
| 3 | A1 | B1 | —(CH₂)₅— | | a | mp = 277–230° C.; ES MS[M+H]⁺=371; TLC: R_f = 0.21(CH₂Cl₂—MeOH, 95:5). |
| 4 | A2 | B1 | —CH₂CH₂N(Bn)CH₂— | | a | mp = 227–230° C.; ES MS(M+H)⁺=448; TLC: R_f = 0.45(CH₂Cl₂—MeOH, 95:5). |
| 5 | A1 | B1 | —(CH₂)₅— | | b | mp = 220–224° C., ES MS[M + H]⁺ = 364; TLC: R_f = 0.39(CH₂Cl₂—MeOH, 95:5). |
| 6 | A1 | B2 | CF₃ | H | c | ¹H NMR(Methanol-d₄)δ8.48–8.50(m, 2H), 8.33(dd, J=1.1, 1.4, 1H), 7.60–7.62(m, 4H), 6.45(s, 1H); ES MS[M + H]⁺ = 382; TLC: R_f = 0.57(CH₂Cl₂—MeOH, 90:10). |
| 7 | A1 | B1 | —(CH₂)₃— | | c | ¹H NMR(Methanol-d₄)δ8.30(d, J=7.1, 2H), 7.71(t, J=7.8, 1H), 7.29–7.38(m, 4H), 3.02(t, J=7.7, 2H), 2.87(t, J=5.5, 2H), 2.28(quint, J=7.6, 2H); ES MS[M+H]⁺=356; TLC: R_f= 0.34(CH₂Cl₂—MeOH, 90:10). |
| 8 | Aldrich | B1 | H | H | d | ¹H NMR(Acetone-d₆)δ7.80(d, J=7.1, 1H), 7.70(s, 1H), 7.34(d, J=8.4, 2H), 7.10(d, J= 8.8, 2H), 6.91(d, J=8.2, 2H), 6.36(d, J=7.1, 1H)TLC: R_f=0.07(95:5 CH₂Cl₂/MeOH). |
| 9 | A1 | B1 | CH₃CH₂— | H | d | mp = 181–184° C., TLC: R_f = 0.13(95:5 CH₂Cl₂/MeOH). |
| 10 | A1 | B1 | (CH₃)₂CH— | H | d | mp = 86–90° C., TLC: R_f = 0.10(95:5 CH₂Cl₂/MeOH). |
| 11 | A1 | B1 | (CH₃)₃C— | H | d | mp = 95–99° C., TLC: R_f = 0.16(95:5 CH₂Cl₂/MeOH). |
| 12 | A1 | B1 | CH₃— | Cl— | d | mp = 242–245° C., TLC: R_f = 0.32(95:5 CH₂Cl₂/MeOH). |

TABLE 3-continued

| 13 | A1 | B1 | CH₃— | H | e | mp = 209–212° C., TLC: R_f = 0.08(95:5 CH₂Cl₂/MeOH). |
| 14 | A1 | B1 | CH₃— | H | f | mp = 271–274° C., TLC: R_f = 0.05(95:5 CH₂Cl₂/MeOH). |

By selecting combinations of the appropriate Intermediates A1–A21 with Intermediates B1–B 17, a variety of products were prepared in like manner and are described in Examples 15–18

Example 15

Preparation of N-(2-amino-6-methyl-4-pyrimidinyl)-N-[4-(3-pyridinylsulfanyl)phenyl]amine

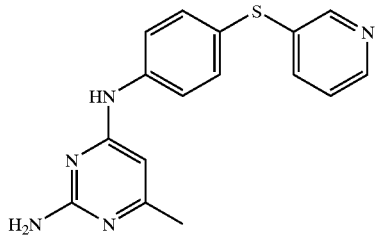

Prepared in 5% yield from A7 and B19: TLC (7% MeOH in CH₂Cl₂) R_f 0.49; MS (ES) 310 [M+H]⁺; ¹H-NMR (DMSO-d₆) δ 2.13 (s, 3H), 5.94 (s, 1H), 6.48 (bs, 2H), 7.31–7.39 (m, 3H), 7.56 (td, J=1.6, 8.2 Hz, 1H), 7.81 (d, J=8.9 Hz, 2H), 8.38–8.40 (m, 2H), 9.50 (bs, 1H).

Example 16

Preparation of N-(2-amino-6-methyl-4-pyrimidinyl)-N-[3-(4-pyridinylsulfanyl)phenyl]amine

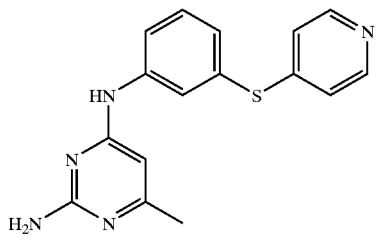

Prepared in 29% yield from A7 and B20: TLC (6% MeOH in CH₂Cl₂) R_f 0.37; MS (ES) 310 [M+H]⁺; ¹H-NMR (DMSO-d₆) δ 2.08 (s, 3H), 5.86 (s, 1H), 6.17 (bs, 2H), 7.06 (d, J=6.0 Hz, 2H), 7.09 (d, J=7.5 Hz, 1H), 7.39 (t, J=7.8 Hz, 1H), 7.78 (t, J=2.2 Hz, 1H), 7.99 (dd, J=1.4, 8.1 Hz, 1H), 8.36 (d, J=6.3 Hz, 2H), 9.18 (bs, 1H).

Example 17

Preparation of N-(2-anilino-6-methyl-4-pyrimidinyl)-N-[4-(4-pyridinylsulfanyl)phenyl]amine

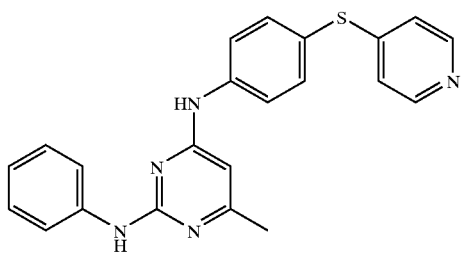

Prepared in 1% yield from A16 and B5: TLC(50% EtOAc/50% hexanes) R_f 0.15; MS (ES) 386 [M+H]⁺; ¹H-NMR (DMSO-d₆) δ 2.25 (s, 3H), 6.14 (s, 1H), 6.89 (t, J=7.4 Hz, 1H), 6.97 (d, J=5.7 Hz, 2H), 7.23 (t, J=7.2 Hz, 2H), 7.47 (d, J=9.0 Hz, 2H), 7.71 (dd, J=0.9, 8.6 Hz, 2H), 7.89 (d, J=8.5 Hz, 2H), 8.33 (bs, 2H), 9.21 (s, 1H), 9.55 (s, 1H).

Example 18

Preparation of N-(2-amino-6-methyl-4-pyrimidinyl)-N-[4-(5-quinolinyloxy)phenyl]amine

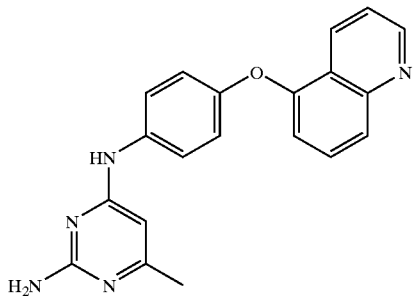

Prepared in 71% yield from A7 and B21: TLC (6% MeOH in CH₂Cl₂) R_f 0.34; MS (ES) 344 [M+H]⁺; ¹H-NMR (DMSO-d₆) δ2.08 (s, 3H), 5.85 (s, 1H), 6.11 (bs, 2H), 6.88 (d, J=7.3 Hz, 1H), 7.04 (d, J=8.6 Hz, 2H), 7.56 (dd, J=4.0, 8.5 Hz, 1H), 7.65 (t, J=8.5 Hz, 1H), 7.73–7.76 (m, 3H), 8.57 (d, J=8.6 Hz, 1H), 8.94 (d, J=3.9 Hz, 1H), 9.03 (bs, 1H).

Examples 19–22

Using the following general method, Examples 19–22 were prepared

A suspension of Intermediate A (1.0 mmol), Intermediate B (1.0 mmol), and HCl (0.1 mL) in H₂O (1.0 mL) was heated to 70° C. in a 5 mL reaction vial overnight. The reaction mixture was diluted with MeOH, treated with saturated NaHCO₃, coated on silica and purified by MPLC (Biotage) with 5% MeOH in CH₂Cl₂.

Example 19

Preparation of N-(2-amino-6-phenyl-4-pyrimidinyl)-N-[3,5-dichloro-4-(4-pyridinylsulfanyl)phenyl]amine

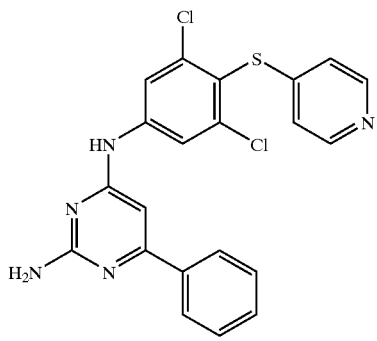

Prepared in 40% yield from A17 and B14: TLC (4% MeOH in CH$_2$Cl$_2$) R$_f$0.42; MS (ES) 440 [M+H]$^+$; $^1$H-NMR (DMSO-d$_6$) δ 6.53 (s, 1H), 6.67 (bs, 2H), 6.94 (d, J=6.1 Hz, 2H), 7.47–7.51 (m, 3H), 7.93–7.96 (m, 2H), 8.18 (s, 2H), 8.36 (d, J=5.7 Hz, 2H), 9.88 (bs, 1H).

Example 20

Preparation of N-[2-amino-6-(3-nitrophenyl)-4-pyrimidinyl]-N-[3-fluoro-4-(4-pyridinylsulfanyl)phenyl]amine

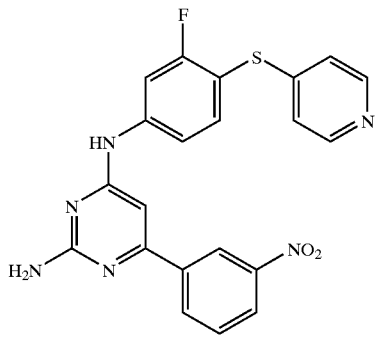

Prepared in 97% yield from A20 and B7: TLC (50% EtOAc/50% hexanes) R$_f$0.15; MS (ES) 435 [M+H]$^+$; $^1$H-NMR (DMSO-d$_6$) δ 6.69 (s, 1H), 6.78 (bs, 2H), 6.98 (d J=4.8 Hz, 2H), 7.46–7.57 (m, 2H), 7.79 (t, J=7.9 Hz, 1H), 8.33–8.35 (m, 5H), 8.79 (s, 1H), 9.94 (bs, 1H).

Example 21

Preparation of N-[2-amino-6-(2-furyl)-4-pyrimidinyl]-N-[3-fluoro-4-(4-pyridinylsulfanyl)phenyl]amine

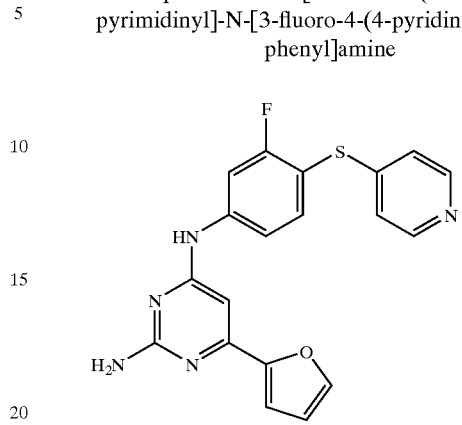

Prepared in 12% yield from A4 and B7: TLC (6% MeOH in CH$_2$Cl$_2$) R$_f$0.37; MS (ES) 380 [M+H]$^+$; $^1$H-NMR (DMSO-d$_6$) δ 6.45 (s, 1H), 6.58 (bs, 2H), 6.64 (dd, J=1.9, 3.5 Hz, 1H), 6.97–6.70 (m, 3H), 7.44 (dd, J=1.9, 8.4 Hz, 1H), 7.53 (t, J=8.6 Hz, 1H), 7.84 (d, J=1.6 Hz, 1H), 8.29–8.35 (m, 3H), 9.80 (bs, 1H).

Example 22

Preparation of N-[2-amino-6-(2-thienyl)-4-pyrimidinyl]-N-[3-fluoro-4-(4-pyridinylsulfanyl)phenyl]amine

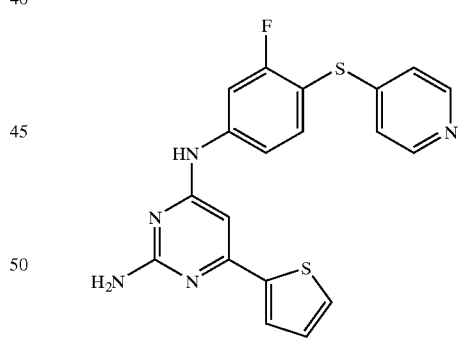

Prepared in 29% yield from A3 and B7. TLC (4% MeOH in CH$_2$Cl$_2$) R$_f$0.22; MS (ES) 396 [M+H]$^+$; $^1$H-NMR (DMSO-d$_6$) δ 6.47 (s, 1H), 6.61 (bs, 2H), 6.98 (d, J=6.4 Hz, 2H), 7.15–7.18 (m, 1H), 7.43–7.68 (m, 4H), 8.29–8.36 (m, 3H), 9.79 (bs, 1H), Using analogous methods, Example 23 is synthesized from 4-chloro-6-furan-3-yl-2-methyl-pyrimidine and Intermediate B7.

Example 23

Preparation of 6-furan-3-yl-N⁴-[4-(pyridin-4-yl-sulfanyl)-phenyl]-pyrimidine-2,4-diamine

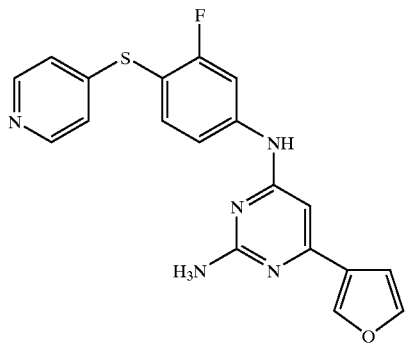

Examples 24–26

The following general procedure and the appropriate Intermediates A and B provided the compounds described in Table 4 below.

A mixture of Intermediate B (0.250 mmol) and Intermediate (0.25 mmol) in 0.01 M aqueous HCl (500 µL) was refluxed for 6 h. The reaction was cooled to room temperature and the solvent was evaporated by vacuum. The residue was purified by reverse phase chromatography on a YMC Pack-pro® C18 column eluting with acetonitrile/H₂O (10:90–90:10 gradient) to give the desired compound.

In some cases, the compound was further purified by preparative TLC eluting with CH₂Cl₂—MeOH (90:10) to give the desired product.

TABLE 4

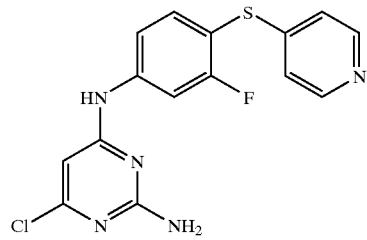

| Ex. No. | Yield % | A int. | B int. | $R_5$ | $R_1$ | $R_2$ | Note |
|---|---|---|---|---|---|---|---|
| 24 | 10 | A13 | B5 | H | —(CH₂)₅— | | 1 |
| 25 | 8 | A6 | B7 | F | CF₃ | H | 2 |
| 26 | 33 | A14 | B7 | F | —(CH₂)₃— | | 3 |

1) mp = 220–224° C., ES MS[M + H]⁺ = 364; TLC(CH₂Cl₂—MeOH, 95:5; $R_f$ = 0.39.
2) ¹H NMR(Methanol-d₄)δ8.48–8.50(m, 2H), 8.33(dd, J=1.1, 1.4, 1H), 7.60–7.62(m, 4H), 6.45(s, 1H); ES MS[M + H]⁺ = 382; TLC(CH₂Cl₂—MeOH, 90:10); $R_f$ = 0.57.
3) ¹H NMR(Methanol-d₄)δ8.30(d, J=7.1, 2H), 7.71(t, J=7.8, 1H), 7.29–7.38(m, 4H), 3.02(t, J=7.7, 2H), 2.87(t, J=5.5, 2H), 2.28(quint, J=7.6, 2H); ES MS[M + H]⁺ = 356; TLC: $R_f$ = 0.34(CH₂Cl₂—MeOH, 90:10).

Example 27

Preparation of N-[2-amino-6-(4-ethoxyphenyl)-4-pyrimidinyl]-N-[3-fluoro-4-(4-pyridinylsulfanyl)phenyl]amine

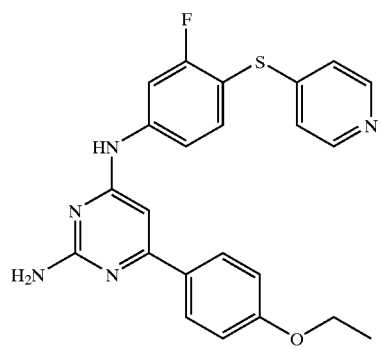

Step 1. Preparation of N-(2-amino-6-chloro-4-pyrimidinyl)-N-[3-fluoro-4-(4-pyridinylsulfanyl)phenyl]amine

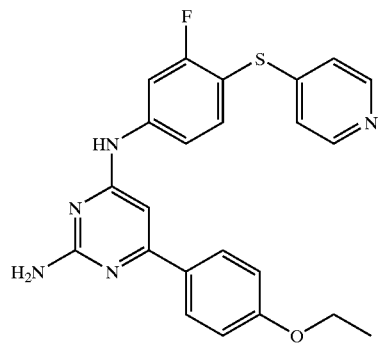

2-Amino-4,6 dichloropyrimidine (A21, 12 mmol) and 3-fluoro-4-(4-pyridinylthio)-aniline (B7,12 mmol) were suspended in water (150 mL) and treated with 10 drops of concentrated hydrochloric acid. The mixture was stirred at 100° C. overnight. The clear solution was then neutralized with ammonium hydroxide. The precipitated yellow product was filtered, washed with water, and purified by column chromatography with 1–3% MeOH in CH₂Cl₂ to give the desired product as a white solid (1.98 g, 47%).

Step 2. Preparation of N-[2-amino-6-(4-ethoxyphenyl)-4-pyrimidinyl]-N-[3-fluoro-4-(4-pyridinylsulfanyl)phenyl]amine A solution of N-(2-amino-6-chloro-4-pyrimidinyl)-N-[3-fluoro-4-(4-pyridinylsulfanyl)phenyl]amine from step 1 in toluene (2 mL) in ethanol (1 mL) was treated with aqueous sodium carbonate solution (2M, 0.5 mL). The mixture was then treated with 4-ethoxyphenylboronic acid (0.36 mmol), tetrakis(triphenylphosphine)-palladium (0.009 mmol), and allowed to stir at 120° C. under argon overnight. At this time, the solvents were removed at reduced pressure and the residue was purified by preparative silica gel with 3% MeOH in $CH_2Cl_2$ to afford the desired product as a white solid (21 mg).

Parallel Synthesis Methods

Examples 28–33

An equivalent of N-(2-amino-6-chloro-4-pyrimidinyl)-N-[3-fluoro-4-(4-pyridinylsulfanyl)phenyl]amine (Example 26, step 1, 0.1 mmol) and four equivalents of the desired amine ($R_6R_7NH$) were suspended in n-butanol (1 mL) and shaken at 110° C. overnight to 2 days. The solvent was removed at reduced pressure and the residue was purified either by preparative silica gel plate or by HPLC. The products were checked by LC-MS and TLC and are listed in Table 5 below.

TABLE 5

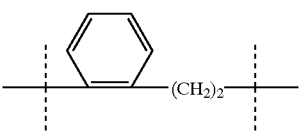

| Ex No. | $R_6$ | $R_7$ |
|---|---|---|
| 28 | —($CH_2CH(Me)OCH(Me)CH_2$— | |
| 29 | —(phenyl)—($CH_2$)$_2$— | |
| 30 | n-Pr | n-Pr |
| 31 | —($CH_2CH_2OCH_2CH_2$— | |
| 32 | i-Pr | H |
| 33 | cyc-Pent | H |

Example 34

Preparation of N-[2-amino-6-(3-aminophenyl)-4-pyrimidinyl]-N-[3-fluoro-4-(4-pyridinylsulfanyl)phenyl]amine

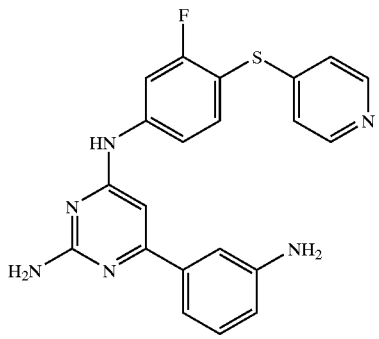

A dry flask under argon was charged with 10% palladium on carbon (20 mg). A solution of N-[2-amino-6-(3-nitrophenyl)-4-pyrimidinyl]-N-[3-fluoro-4-(4-pyridinylsulfanyl)phenyl]amine (Example 20, 200 mg, 0.46 mmol) in ethanol (12 mL) and EtOAc (1 mL) was added via syringe through a septa to the palladium on carbon. The flask was then fitted with a hydrogen balloon and stirred at room temperature for 48 h. At this time the palladium was filtered through a pad of Celite®. The filtrate was coated on silica and purified on the MPLC (Biotage) with 2–8% MeOH in $CH_2Cl_2$ to afford the desired product as a solid (120 mg, 64%). TLC (6% MeOH in $CH_2Cl_2$) $R_f$ 0.26; MS (ES) 405 [M+H]$^+$; $^1$H-NMR (DMSO-$d_6$) δ 5.22 (bs, 2H), 6.45 (s, 1H), 6.49 (bs, 2H) 6.62–6.65 (m, 1H), 6.98 (d, J=6.4 Hz, 2H), 7.02–7.16 (m, 3H), 7.43–7.55 (m, 2H), 8.30–8.35 (m, 3H), 9.75 (bs, 1H).

Examples 35 to 41 listed in the table below can be prepared analogously to the procedure described in Example 1 using the following starting materials:

| Example | starting material 1 | starting material 2 |
|---|---|---|
| 35 | B7 or C4 | 2,4-diamino-6-chloro-pyrimidine |
| 36 | B7 or C4 | 2-amino-4-chloro-6-N-methylamino-pyrimidine* |
| 37 | C5 | 2,4-diamino-6-chloro-pyrimidine |
| 38 | C7 | A 21 |
| 39 | C8 | A 21 |
| 40 | C6 | A 2 |
| 41 | C7 | A 2 |

*was internally available, cited in:
DE 839640;
U.S. Pat. No. 2,585,906;
Autenrieth et al., Justus Liebigs Ann. Chem., 1977, 1194, 1210.

| Example | Structure | Analytical data |
|---|---|---|
| 35 | [structure: 4-pyridyl-S-(3-fluoro-phenyl)-NH-pyrimidine-2,6-diamine] | ¹H-NMR(300MHz, DMSO-d₆) δ=5.11(s, 1H), 5.82(d, 2H), 5.95(s, 2H), 6.97(d, 2H), 7.35–7.46(m, 2H), 8.16(dd, 1H), 8.34(d, 2H), 9.12(s, 1H) LC-MS(method 7): RT = 0.43 min MS(ESIpos): m/z = 329 (M + H)⁺ |
| 36 | [structure: 4-pyridyl-S-(3-fluoro-phenyl)-NH-(N-methyl)pyrimidine-2,4-diamine] | ¹H-NMR(200MHz, DMSO-d₅) δ=2.78(d, 3H), 5.19 (s, 1H), 5.76(s, 1H), 5.92(s, 2H), 6.96(d, 2H), 7.32–7.48 (m, 2H), 8.20(dd, 1H), 8.75 (d, 2H), 9.19(s, 1H) MS(ESIpos): m/z = 343 |
| 37 | [structure: isoquinolin-5-yl-O-(3-fluoro-phenyl)-NH-pyrimidine-2,6-diamine] | LC/MS(method 10): RT = 1.37 min. MS(ESI pos.): m/z = 363(M + H)⁺, |
| 38 | [structure: 4-pyridyl-S-(3,5-difluoro-phenyl)-NH-(6-chloro)pyrimidine-2-amine] | MS(ESI pos.): m/z = 366(M + H)⁺, HPLC(method 1): RT = 3.75 min. |
| 39 | [structure: 4-pyridyl-S-(3-chloro-phenyl)-NH-(6-chloro)pyrimidine-2-amine] | LS/MS(method 12): RT = 2.90 min. MS(ESI pos.): m/z = 363(M + H)⁺, |

| Example | Structure | Analytical data |
|---|---|---|
| 40 | 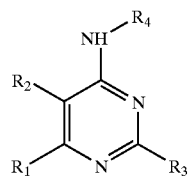 | MS(ESI pos.): m/z = 425(M + H)$^+$, HPLC (method 1): RT = 3.45 min. |
| 41 | 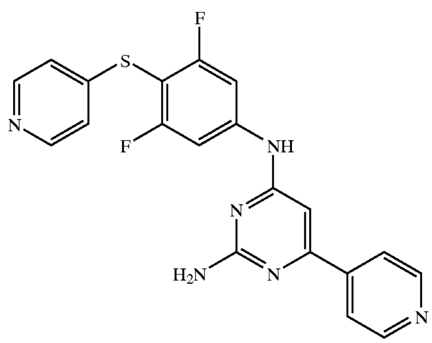 | LC/MS(method 10): RT = 1.59 min. MS(ESI pos.): m/z = 409(M + H)$^+$, 205(M + H)$^{2+}$ |

Rho Kinase Biochemical Assay

ROCK-1 activity criteria: 0 no effect (<40% inhibition), 1 effect (>40% inhibition). The assay tests for inhibition of ROCK-1 phosphorylation of MBP (Myelin Basic Protein). The reaction (100 μl final volume) is carried out in polypropylene 96-well plates in 50 mM HEPES buffer pH 7.5 containing 5 mM MgCl$_2$ and 1 mM DTT. For each well, gstROCK1 (0.25 μgs of BAYER DRT gstROCK1) is combined with MBP (1 μg) in reaction buffer (70 μL combined volume). Inhibitors (5 μL of 20× conc. in 40% DMSO) are added to each well to give an 8 point dose response range from 1.0 μM to 0.5 nM. The reaction is begun by adding 25 μL of ATP (4×=12 μM) in reaction buffer containing 0.8 μCi of $^{33}$P gamma-ATP (4×) for a final concentration of 3 μM cold and 0.2 μCi hot ATP. Plates were incubated for 1 hour at room temperature with the reaction being stopped by addition of 7 μL of 1 N HCl. The radioactively labeled MBP was transferred to P30 filtermats (EG&G Wallac), washed in 1% phosphoric acid followed by brief washes in water. The filtermats were then dried and the incorporation of $^{33}$P detected by liquid scintillation counting. Background $^{33}$P incorporation is determined by ROCK1 autophosphorylation without MBP. The data are expressed as percent inhibition:

% inhibition=1−((*cpm* with inhibitor−background)/(*cpm* without inhibitor−background))*100.

What we claim:

1. A compound of formula I:

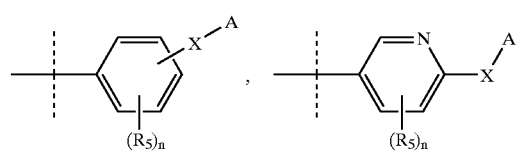

wherein R$_1$ and R$_2$ are each independently

H, halo, alkyl optionally substituted by halo up to perhalo, cycloalkyl, alkenyl, alkynyl, NO$_2$, NH$_2$, NR$_6$R$_7$, or furyl, thienyl, pyridyl, trifluoromethyl or phenyl each optionally substituted with NH$_2$, NO$_2$, trifluoromethyl or alkoxy; or R$_1$ and R$_2$ may be taken together to form a ring of from 5 to 7 members optionally interrupted by N and optionally substituted on N by benzyl;

R$_3$ is NH$_2$ or —NH-phenyl optionally substituted with halo, C$_1$–C$_4$ alkyl, trifluoromethyl, nitro or amino;

R$_4$ is or indol-5-yl (optionally) substituted on N with pyridyl;

X is a linker substituted at the 3 or 4 position of the ring and is O, S, —S—CH$_2$—, —(CH$_2$)m—, or —(C=O)—;

A is phenyl, phenyl substituted with alkylthio or OH,
pyridyl,
quinolyl or
isoquinolyl;

each R$_5$ independently is halo, alkyl optionally substituted by halo up to perhalo, cycloalkyl, alkoxy, alkenyl, alkynyl, NO$_2$, NH$_2$, or trifluoromethyl;

n is 0, 1, 2, 3 or 4;

m is 1 or 2; and

R$_6$ and R$_7$ are each independently H, alkyl, cycloalkyl, or phenyl optionally substituted with halo, CF$_3$, alkyl, nitro or amino; or R$_6$ and R$_7$ may form, together with the N atom to which they are attached, a heterocyclic ring optionally substituted with alkyl, optionally interrupted by O, or optionally fused to phenyl;

or a pharmaceutically acceptable salt thereof, with the proviso that formula I does not include the following compounds:

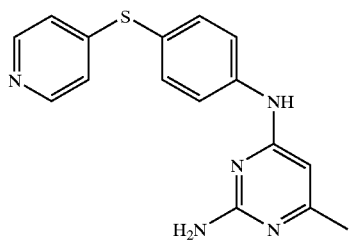

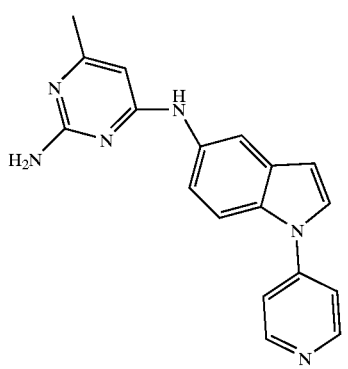

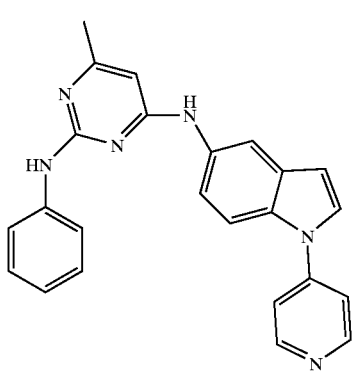

-continued

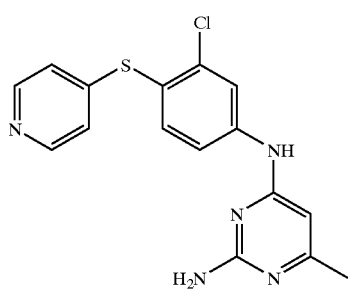

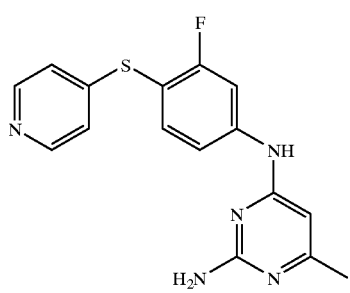

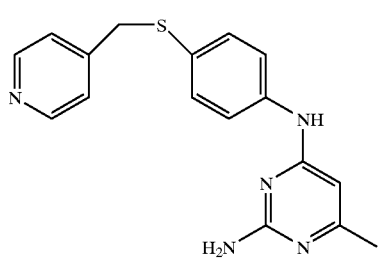

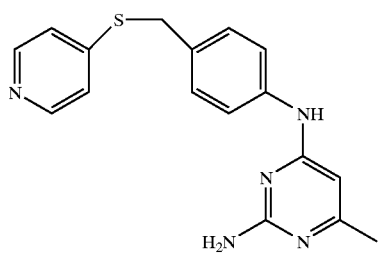

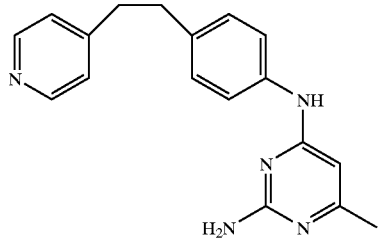

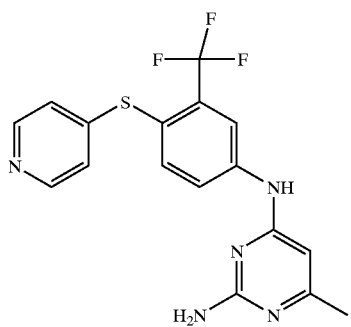
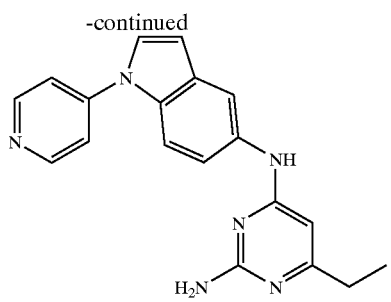
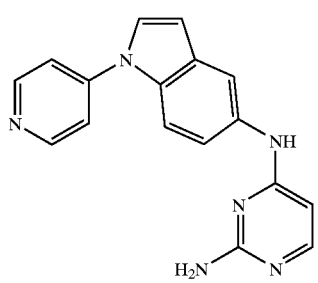
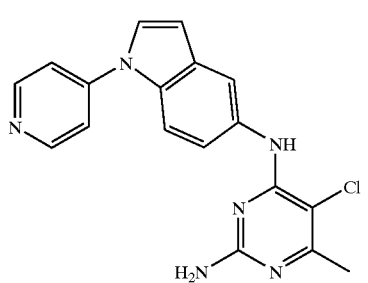
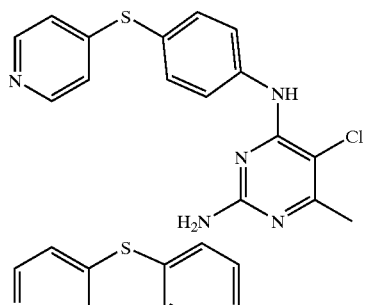
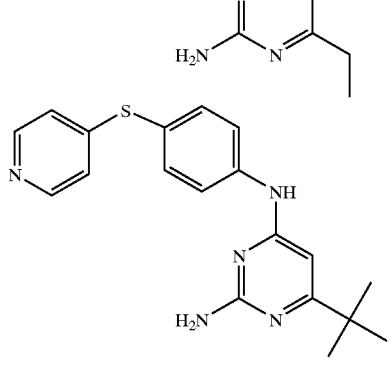

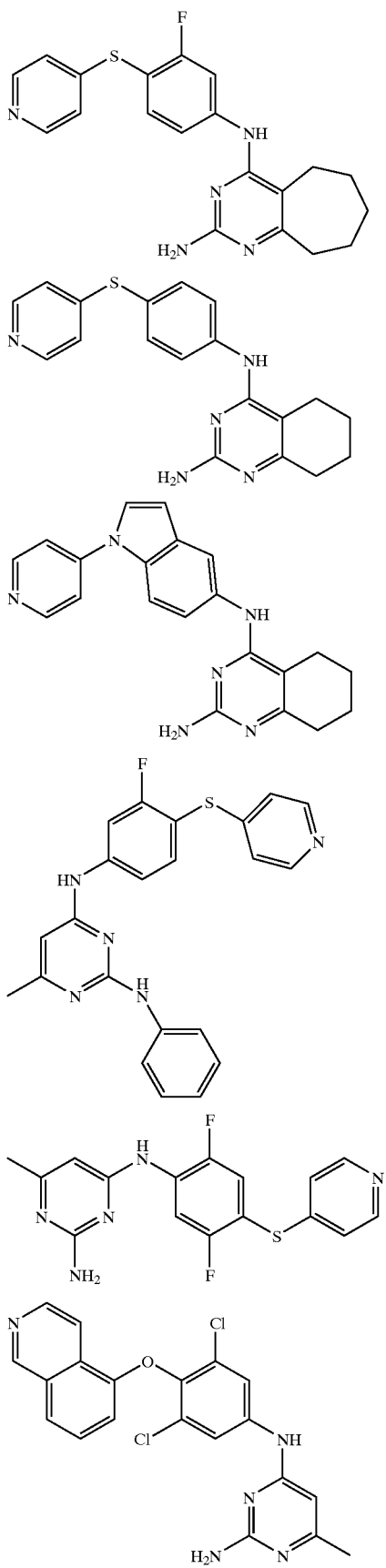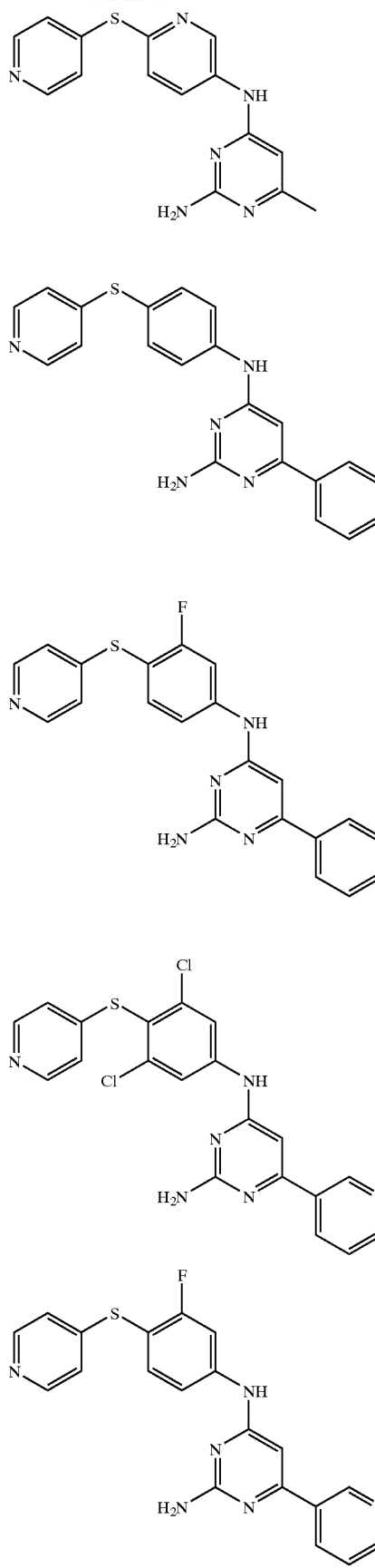

-continued
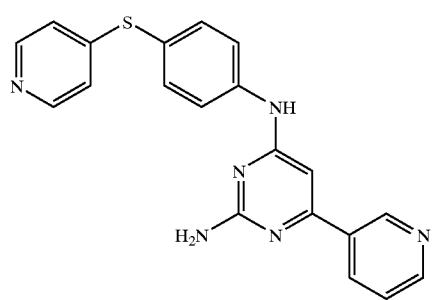
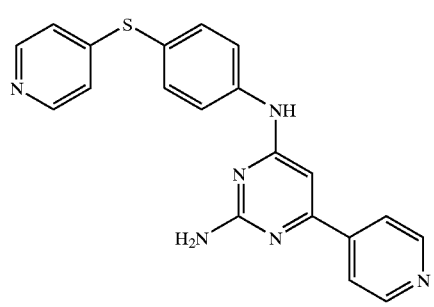
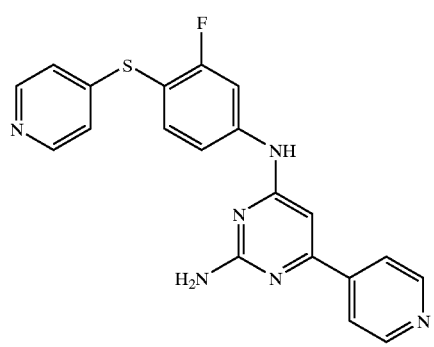
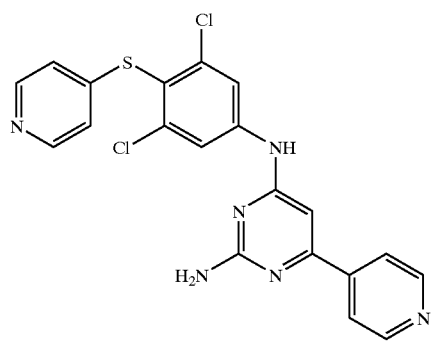
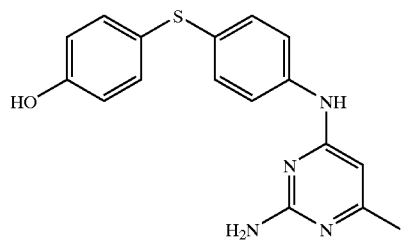
-continued
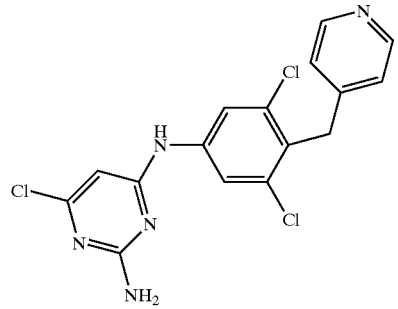
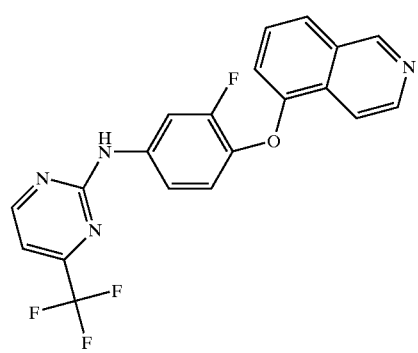
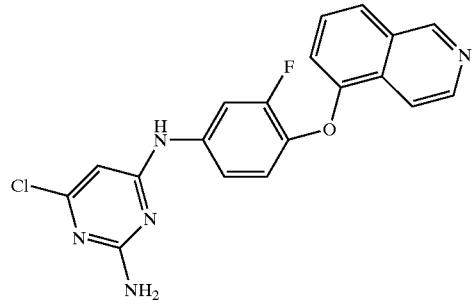
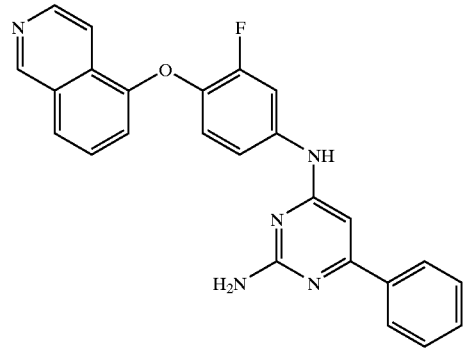
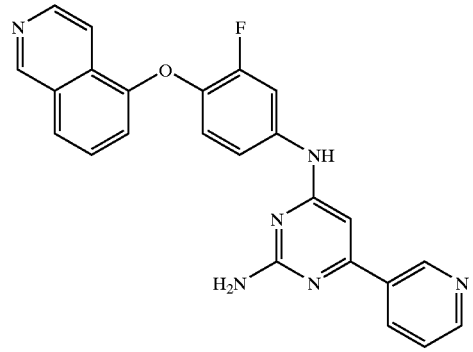

-continued

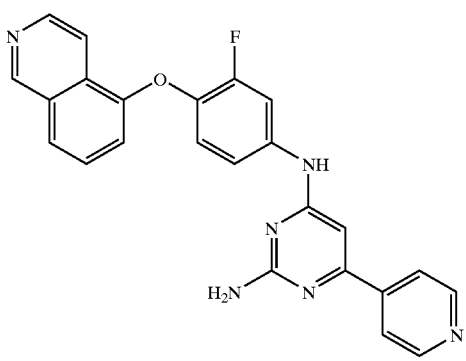

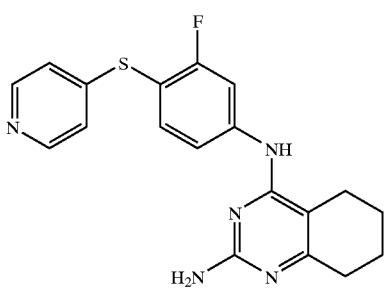

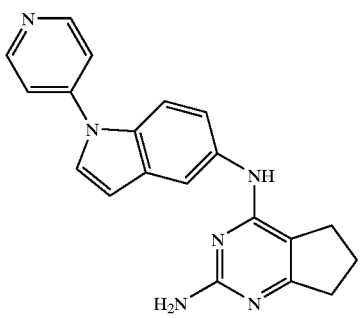

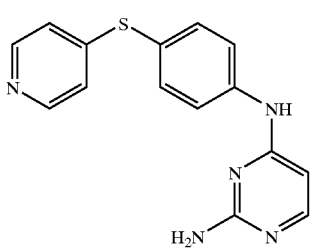

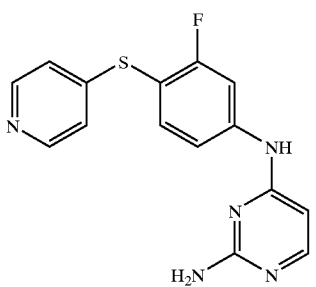

-continued

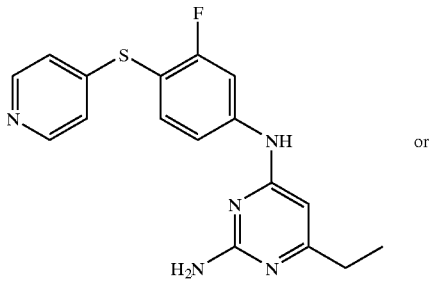

or

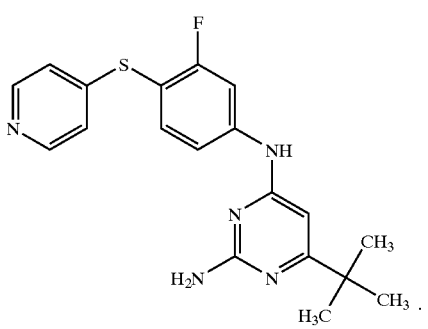

2. A compound of formula I according to claim 1, wherein
$R_1$ and $R_2$ are each independently H, halo, $C_{1-12}$-alkyl optionally substituted by halo up to perhalo, $C_{2-12}$-alkenyl, $C_{2-12}$-alkynyl, $NO_2$, $NH_2$, $NR_6R_7$, alkyl, furyl, thienyl, pyridyl, phenyl optionally substituted with $NO_2$, trifluoromethyl or $NR_6R_7$; or $R_1$ and $R_2$ together form a ring of from 5 to 7 members optionally interrupted by N and optionally substituted on N by benzyl;

$R_3$ is $NH_2$ or —NH-phenyl optionally substituted with halo, $C_1$–$C_4$ alkyl, trifluoromethyl, nitro or amino;

$R_4$ is

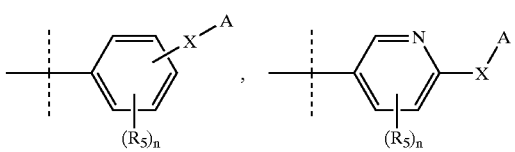

or indol-5-yl (optionally) substituted on the N with pyridyl;

X is a linker substituted at the 3 or 4 position of the ring and is selected from O, S, —S—$CH_2$—, —$CH_2$—S—, —($CH_2$)m—, or —(C=O)—;

A is phenyl, phenyl substituted by $C_{1-4}$ alkylthio or OH, pyridyl, quinolyl or isoquinolyl;

each $R_5$ independently is halo, $C_1$–$C_{12}$ alkyl, optionally substituted by halo, up to the perhalo level, $C_{2-12}$-alkenyl, $C_{2-12}$-alkynyl, $NO_2$, $NH_2$ or trifluoromethyl;

n is 0, 1, 2, 3 or 4;

m is 1 or 2; and $R_6$ and $R_7$ are each independently H, $C_1$–$C_6$ alkyl, or phenyl optionally substituted with halo, $CF_3$, $C_1$–$C_4$ alkyl, nitro or amino.

3. A compound according to claim 1, wherein X is not S or A is not pyridyl.

4. A compound according to claim 1, wherein X is not S or —S—CH$_2$.

5. A compound according to claim 1, wherein n is 1–4.

6. A compound according to claim 1, wherein n is 1–4 and each R$_5$ is independently halo, C$_3$–C$_{12}$ alkyl optionally substituted by halo up to the perhalo level, C$_{2-12}$-alkenyl, C$_{2-12}$-alkynyl, NO$_2$, NH$_2$ or trifluoromethyl.

7. A compound according to claim 1, which is 6-tert-butyl-N$^4$-(1-pyridin-4-yl-1H-indol-5-yl)-pyrimidine-2,4-diamine , N$^4$-(1-pyridin-4-yl-1H-indol-5-yl)-6,7,8,9-tetrahydro-5H-cycloheptapyrimidine-2,4-diamine, 7-benzyl-N$^4$-(1-pyridin-4-yl-1H-indol-5-yl)-5,6,7,8-tetrahydro-pyrido[3,4-d]pyrimidine-2,4-diamine, N$^4$-[4-(pyridin-4-ylsulfanyl)-phenyl]-6,7,8,9-tetrahydro-5H-cycloheptapyrimidine-2,4-diamine, N$^4$-[3-fluoro-4-(pyridin-4-ylsulfanyl)-phenyl]-6-trifluoromethyl-pyrimidine-2,4-diamine, N$^4$-[3-fluoro-4-(pyridin-4-ylsulfanyl)-phenyl]-6,7-dihydro-5H-cycloheptapyrimidine-2,4-diamine, 4-[4-(2-amino-pyrimidin-4-ylamino)-phenylsulfanyl]-phenol, 4-[4-(2-amino-6-ethyl-pyrimidin-4-ylamino)-phenylsulfanyl]-phenol, 4-[4-(2-amino-6-isopropyl-pyrimidin-4-ylamino)-phenylsulfanyl]-phenol, 4-[4-(2-amino-6-tert-butyl-pyrimidin-4-ylamino)-phenylsulfanyl]-phenol, 4-[4-(2-amino-5-chloro-6-methyl-pyrimidin-4-ylamino)-phenylsulfanyl]-phenol, [3-(2-amino-5-chloro-6-methyl-pyrimidin-4-ylamino)-phenyl]-(4-methylsulfanyl-phenyl)-methanone, 4-[4-(2-amino-5-chloro-6-methyl-pyrimidin-4-ylamino)-phenoxy]-phenol, N$^4$-[4-(pyridin-4-ylsulfanyl)-phenyl]-6,7,8,9-tetrahydro-5H-cycloheptapyrimidine-2,4-diamine, N$^4$-[3-fluoro-4-(pyridin-4-ylsulfanyl)-phenyl]-6-trifluoromethyl-pyrimidine-2,4-diamine, N$^4$-[3-fluoro-4-(pyridin-4-ylsulfanyl)-phenyl]-6,7-dihydro-5H-cyclopentapyrimidine-2,4-diamine, 6-(2,6-dimethyl-morpholin-4-yl)-N$^4$-[3-fluoro-4-(pyridin-4-ylsulfanyl)-phenyl]-pyrimidine-2,4-diamine, 6-(2,3-dihydro-indol-1-yl)-N$^4$-[3-fluoro-4-(pyridin-4-ylsulfanyl)-phenyl]-pyrimidine-2,4-diamine, N'-[3-fluoro-4-(pyridin-4-ylsulfanyl)-phenyl]-N'',N''-dipropyl-pyrimidine-2,4,6-triamine, N$^4$-[3-fluoro-4-(pyridin-4-ylsulfanyl)-phenyl]-6-morpholin-4-yl-pyrimidine-2,4-diamine, N'-[3-fluoro-4-(pyridin-4-ylsulfanyl)-phenyl]-N''-isopropyl-pyrimidine-2,4,6-triamine, N'-cyclopentyl-N''-[3-fluoro-4-(pyridin-4-ylsulfanyl)-phenyl]-pyrimidine-2,4,6-triamine, 4-({4-[(2-amino-6-ethyl-4-pyrimidinyl)amino]phenyl}sulfanyl)phenol, N-(2-amino-6-methyl-4-pyrimidinyl)-N-[4-(3-pyridinylsulfanyl)phenyl]amine, N-(2-amino-6-methyl-4-pyrimidinyl)-N-[3-(4-pyridinylsulfanyl)phenyl]amine, N-(2-anilino-6-methyl-4-pyrimidinyl)-N-[4-(4-pyridinylsulfanyl)phenyl]amine, N-(2-amino-6-methyl-4-pyrimidinyl)-N-[4-(5-quinolinyloxy)phenyl]amine, N-(2-amino-6-phenyl-4-pyrimidinyl)-N-[3,5-dichloro-4-(4-pyridinylsulfanyl)phenyl]amine, N-[2-amino-6-(3-nitrophenyl)-4-pyrimidinyl]-N-[3-fluoro-4-(4-pyridinylsulfanyl)phenyl]amine, N-[2-amino-6-(2-furyl)-4-pyrimidinyl]-N-[3-fluoro-4-(4-pyridinylsulfanyl)phenyl]amine, N-[2-amino-6-(2-thienyl)-4-pyrimidinyl]-N-[3-fluoro-4-(4-pyridinylsulfanyl)phenyl]amine, or N-[2-amino-6-(4-ethoxyphenyl)-4-pyrimidinyl]-N-[3-fluoro-4-(4-pyridinylsulfanyl)phenyl]amine.

8. A compound according to claim 1, of the formula:

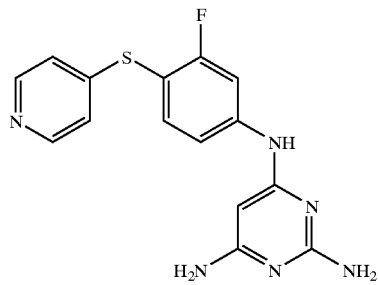

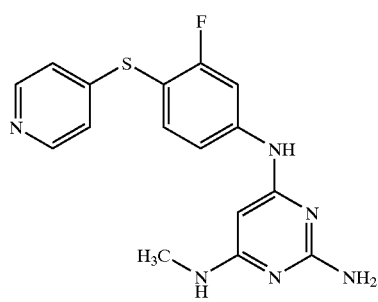

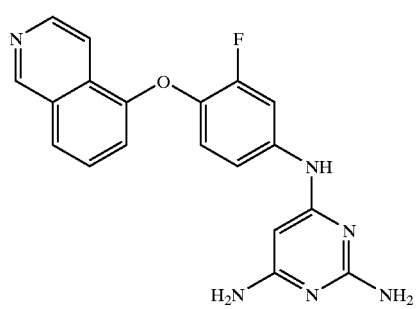

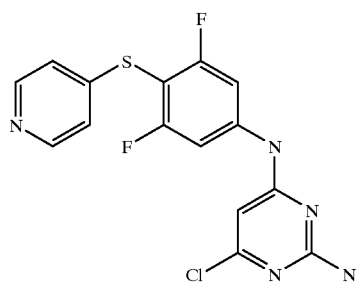

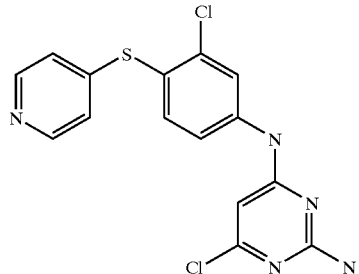

-continued

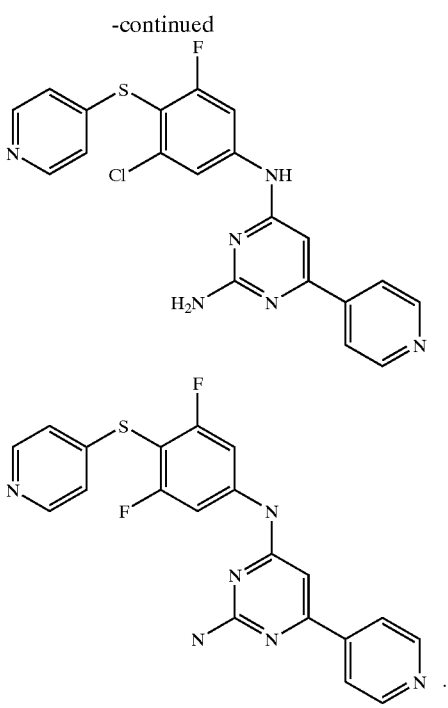

9. A compound according to claim 1, of the formula:

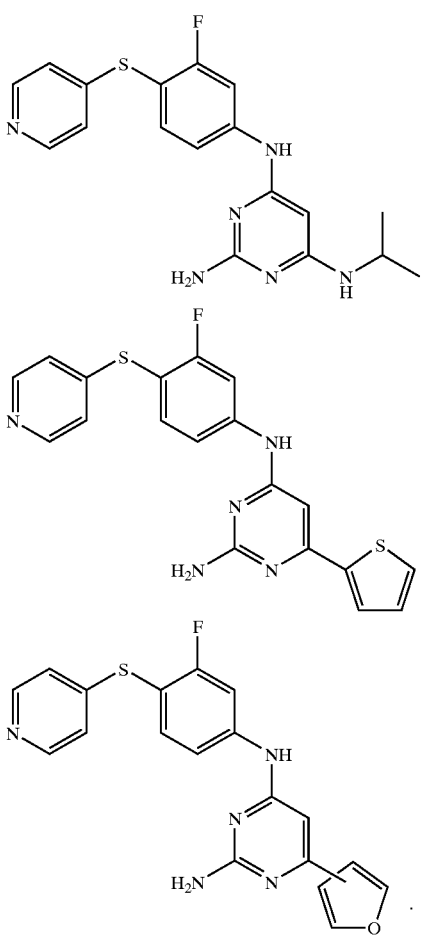

10. A compound according to claim 1, of the formula:

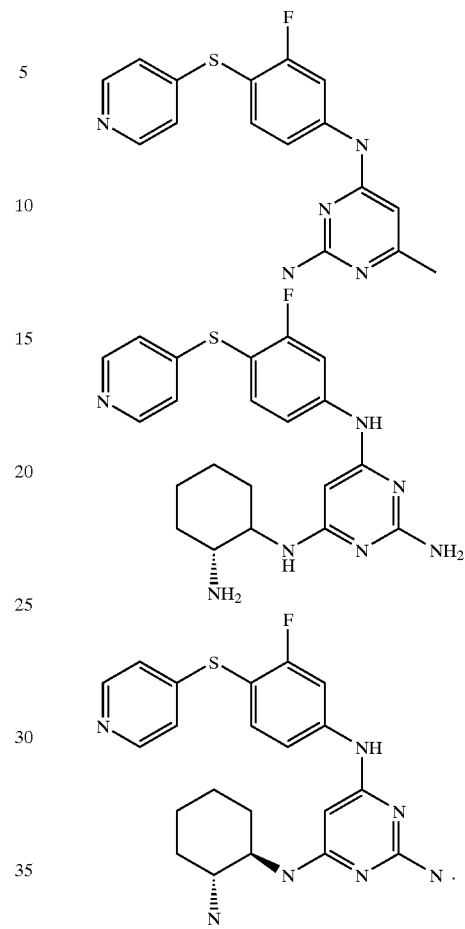

11. A method of treating an indication mediated by Rho-kinase, comprising administering a compound of claim 1.

12. A method of treating hypertension, atherosclerosis, restenosis, cerebral ischemia, cerebral vasospasm, neuronal degeneration, spinal cord injury, cancer of the breast, colon, prostate, ovaries, brain or lung, thrombotic disorders, asthma, glaucoma, osteoporosis or erectile dysfunction, comprising administering to host in need thereof a compound according to claim 1.

13. A process according to claim 11, wherein the host is a human.

14. A process according to claim 12, wherein the host is a human.

15. A process for the preparation of a compound of claim 1, comprising reacting a)

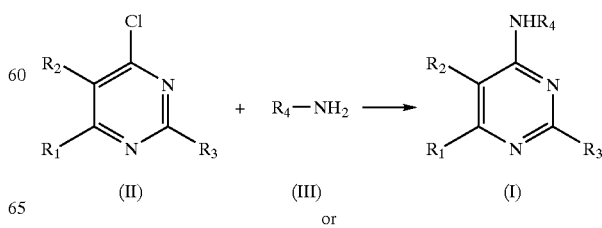

or b)
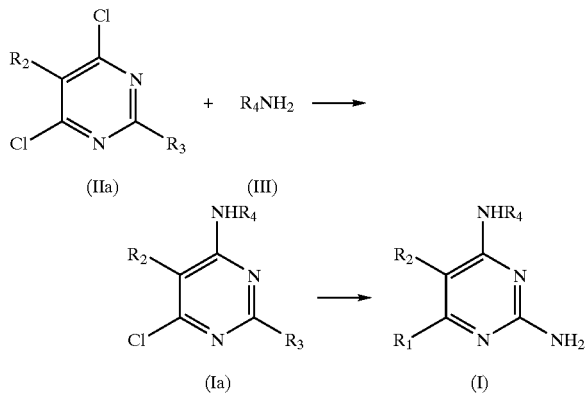
and optionally, where $R_1$ is $NR_6R_7$, reacting the chloropyrimidine of Formula Ia with an amine of Formula $R_6R_7NH$.
16. A method of treating atherosclerosis, comprising administering a compound of claim 1.
17. A method of treating hypertension, comprising administering a compound of claim 1.
* * * * *

UNITED STATES PATENT AND TRADEMARK OFFICE
CERTIFICATE OF CORRECTION

PATENT NO. : 6,924,290 B2
APPLICATION NO. : 10/349177
DATED : August 2, 2005
INVENTOR(S) : Dhanapalan Nagarathnam et al.

It is certified that error appears in the above-identified patent and that said Letters Patent is hereby corrected as shown below:

Column 58, top diagram, line 2, reads

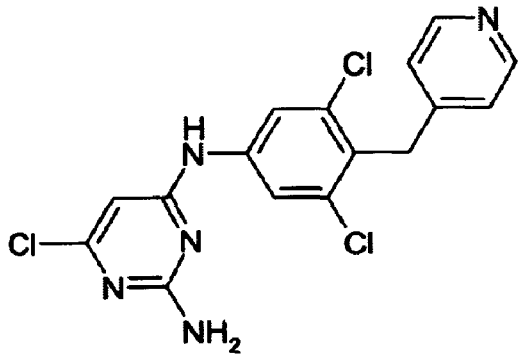

place S as shown.

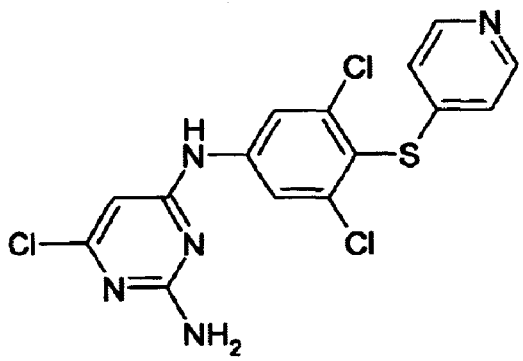

UNITED STATES PATENT AND TRADEMARK OFFICE
CERTIFICATE OF CORRECTION

PATENT NO. : 6,924,290 B2
APPLICATION NO. : 10/349177
DATED : August 2, 2005
INVENTOR(S) : Dhanapalan Nagarathnam et al.

It is certified that error appears in the above-identified patent and that said Letters Patent is hereby corrected as shown below:

Column 64, third diagram, line 30 reads

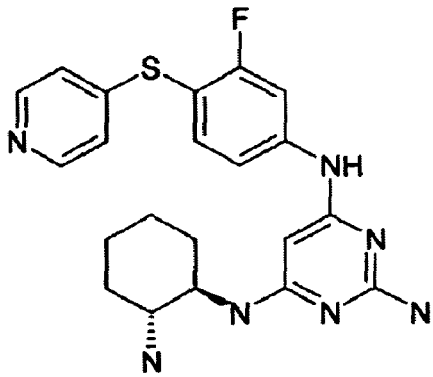

remove H as shown

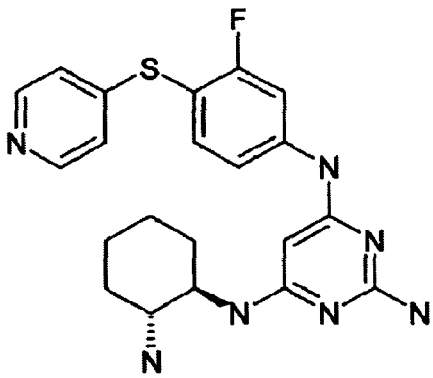

Signed and Sealed this

Seventeenth Day of October, 2006

JON W. DUDAS
*Director of the United States Patent and Trademark Office*